US012773096B2

(12) United States Patent
Enomoto et al.

(10) Patent No.: US 12,773,096 B2
(45) Date of Patent: Oct. 27, 2026

(54) ENDOSCOPE AND METHOD FOR PRODUCING ENDOSCOPE

(71) Applicant: i-PRO CO., LTD., Tokyo (JP)

(72) Inventors: Hirofumi Enomoto, Fukuoka (JP); Naoyuki Haraguchi, Fukuoka (JP); Yuichi Hatase, Fukuoka (JP)

(73) Assignee: i-PRO CO., LTD., Tokyo (JP)

( * ) Notice: Subject to any disclaimer, the term of this patent is extended or adjusted under 35 U.S.C. 154(b) by 251 days.

(21) Appl. No.: 18/576,433

(22) PCT Filed: Jun. 29, 2022

(86) PCT No.: PCT/JP2022/026092
§ 371 (c)(1),
(2) Date: Jan. 4, 2024

(87) PCT Pub. No.: WO2023/282159
PCT Pub. Date: Jan. 12, 2023

(65) Prior Publication Data

US 2024/0315534 A1 Sep. 26, 2024

(30) Foreign Application Priority Data

Jul. 7, 2021 (JP) ................................ 2021-113080

(51) Int. Cl.
*A61B 1/00* (2006.01)

(52) U.S. Cl.
CPC ........ *A61B 1/00096* (2013.01); *A61B 1/0011* (2013.01)

(58) Field of Classification Search
CPC ............................ A61B 1/00096; H04N 23/54
See application file for complete search history.

(56) References Cited

U.S. PATENT DOCUMENTS

2003/0171649 A1 9/2003 Yokoi et al.
2005/0179805 A1* 8/2005 Avron .................... A61B 1/051 348/340

(Continued)

FOREIGN PATENT DOCUMENTS

JP 2003-260023 9/2003
JP 2005-74035 3/2005

(Continued)

OTHER PUBLICATIONS

International Search Report issued in International Patent Application No. PCT/JP2022/026092, dated Sep. 13, 2022.

(Continued)

*Primary Examiner* — Alireza Nia
(74) *Attorney, Agent, or Firm* — GREENBLUM & BERNSTEIN, P.L.C.

(57) ABSTRACT

An endoscope include an image sensor having an imaging surface and a lens adhered to the imaging surface by an adhesive and imaging light on the image sensor. The lens includes a light incident surface extending in an orthogonal direction orthogonal to an optical axis direction of the lens, a back surface parallel to the light incident surface and facing the imaging surface, a recess having an opening disposed in the back surface and an in-lens space disposed between the opening and the light incident surface, the recess being recessed from the opening toward the light incident surface, an emission portion disposed in the in-lens space and emitting light from the light incident surface to the imaging surface, a frame portion disposed around the opening in the back surface, and a protrusion protruding from the frame portion in the optical axis direction and abutting on the imaging surface.

18 Claims, 19 Drawing Sheets

(56) References Cited

U.S. PATENT DOCUMENTS

| | | | | |
|---|---|---|---|---|
| 2008/0239525 | A1* | 10/2008 | Chan .................... | G02B 13/001<br>359/829 |
| 2011/0007203 | A1 | 1/2011 | Avron et al. | |
| 2013/0329026 | A1 | 12/2013 | Hida et al. | |
| 2017/0064162 | A1 | 3/2017 | Haraguchi et al. | |
| 2017/0307872 | A1* | 10/2017 | Hatase ................. | A61B 1/0684 |
| 2018/0013936 | A1 | 1/2018 | Haraguchi et al. | |
| 2018/0013937 | A1 | 1/2018 | Haraguchi et al. | |
| 2018/0020134 | A1 | 1/2018 | Haraguchi et al. | |
| 2018/0220051 | A1 | 8/2018 | Yoneyama | |
| 2019/0076002 | A1 | 3/2019 | Shimohata | |
| 2020/0201024 | A1 | 6/2020 | Hatase et al. | |
| 2021/0223535 | A1 | 7/2021 | Hatase et al. | |

FOREIGN PATENT DOCUMENTS

| | | |
|---|---|---|
| JP | 2005-193053 | 7/2005 |
| JP | 2017-46855 | 3/2017 |
| JP | 2017-86550 | 5/2017 |
| JP | 2021-94420 | 6/2021 |
| WO | 2013/031276 | 3/2013 |
| WO | 2013/146091 | 10/2013 |
| WO | 2019210227 | 10/2019 |

OTHER PUBLICATIONS

Written Opinion issued in International Patent Application No. PCT/JP2022/026092, dated Sep. 13, 2022.

Extended European Search Report received in EP Application No. 22837575.4, dated Sep. 27, 2024.

* cited by examiner

SHORT-DISTANCE IMAGING

BRING LENS AND SENSOR CLOSE TO EACH OTHER

ALIGN OPTICAL AXES OF LENS AND SENSOR

ENDOSCOPE AND METHOD FOR PRODUCING ENDOSCOPE

TECHNICAL FIELD

The present disclosure relates to an endoscope and a method for producing the endoscope.

BACKGROUND ART

An endoscope for imaging the inside of a patient's body, a machine, or a structure is widely used in the medical field or the industrial field. In such an endoscope, in an insertion portion to be inserted into an observation target, light from an imaging part of the observation target is imaged on an imaging surface of an image sensor via an objective lens system. For example, in the medical field, in order to reduce a burden on an operation subject such as a patient, it is important to further reduce an outer diameter of an insertion portion of an endoscope to be inserted into the body of the operation subject.

An endoscope disclosed in Patent Literature 1 includes a long and elongated insertion portion. The insertion portion of the endoscope disclosed in Patent Literature 1 includes a distal end portion, a curved portion, and a flexible tube portion in this order from a distal end side to be inserted into an operation subject.

An endoscope disclosed in Patent Literature 2 includes an outer tube at a distal end portion thereof. The outer tube is provided with an imaging mechanism covered with a filled light-shielding material. The imaging mechanism includes an imaging element including a light receiving portion on one surface, a cover member covering the surface of the imaging element on which the light receiving portion is provided, a lens unit optically coupled to the light receiving portion of the imaging element, and a flexible printed wiring board. The lens unit includes, from an objective side, an objective cover member, an aperture, a plane-convex lens, and a lens barrel to which these are fixed. The plane-convex lens and the cover member are fixed by an adhesive.

CITATION LIST

Patent Literature

Patent Literature 1: WO 2013/031276
Patent Literature 2: WO 2013/146091

SUMMARY OF INVENTION

Technical Problem

However, since it is difficult to quantify an adhesion thickness between the lens and the image sensor, it is not easy to control the adhesion thickness between the lens and the image sensor. In particular, in an endoscope having a small diameter of about a submillimeter order, an adhesive force decreases due to variation in the adhesion thickness between the lens and the image sensor. As a result, there is problem in that the lens is likely to be warped, and an image quality of an image captured by the image sensor deteriorates (in other words, the image quality is unstable).

The present disclosure is devised in view of the related-art circumstances described above, and an object thereof is to provide an endoscope capable of preventing deterioration in image quality and a method for producing the endoscope.

Solution to Problem

According to an aspect of the present disclosure, there is provided an endoscope including: an image sensor having an imaging surface; and a lens configured to be adhered to the imaging surface by an adhesive and to image light on the image sensor, and the lens includes a light incident surface extending in an orthogonal direction orthogonal to an optical axis direction of the lens, a back surface parallel to the light incident surface and facing the imaging surface, a recess having an opening formed in the back surface and an in-lens space formed between the opening and the light incident surface, the recess being recessed from the opening toward the light incident surface, an emission portion disposed in the in-lens space and configured to emit light from the light incident surface to the imaging surface, a frame portion disposed around the opening in the back surface, and a protrusion protruding from the frame portion in the optical axis direction and configured to abut on the imaging surface.

According to another aspect of the present disclosure, there is provided an endoscope including: an image sensor including an imaging surface and an element cover glass that covers the imaging surface; and a lens configured to be adhered to the element cover glass by an adhesive and to image light on the image sensor, and the lens includes a light incident surface extending in an orthogonal direction orthogonal to an optical axis direction of the lens, a back surface parallel to the light incident surface and facing the element cover glass, a recess having an opening formed in the back surface and an in-lens space formed between the opening and the light incident surface, the recess being recessed from the opening toward the light incident surface, an emission portion disposed in the in-lens space and configured to emit light from the light incident surface to the imaging surface, a frame portion disposed around the opening in the back surface, and a protrusion protruding from the frame portion in the optical axis direction and configured to abut on the element cover glass.

According to another aspect of the present disclosure, there is provided a method for producing an endoscope including: an image sensor having an imaging surface, and a lens including a frame portion disposed on a back surface facing the imaging surface and a protrusion portion formed at the frame portion, the lens being configured to be adhered to the imaging surface by an adhesive and to image light on the image sensor, and the method includes: an application step of applying the adhesive to either the frame portion or the imaging surface; an optical axis alignment step of aligning an optical axis of the image sensor with an optical axis of the lens; an abutment step of abutting the lens on the imaging surface via the protrusion portion; and a curing step of curing the adhesive.

According to another aspect of the present disclosure, there is provided a method for producing an endoscope including: an image sensor including an imaging surface and an element cover glass that covers the imaging surface, and a lens including a frame portion disposed on a back surface facing the element cover glass and a protrusion portion formed at the frame portion, the lens being configured to be adhered to the element cover glass by an adhesive, and to image light on the image sensor, and the method includes: an application step of applying the adhesive to either the frame portion or the element cover glass; an optical axis alignment step of aligning an optical axis of the image sensor with an optical axis of the lens; an abutment step of abutting the lens on the element cover glass via the protrusion portion; and a curing step of curing the adhesive.

Advantageous Effects of Invention

According to the present disclosure, it is possible to provide the endoscope capable of preventing deterioration in image quality and the method for producing the endoscope.

DESCRIPTION OF EMBODIMENTS

Hereinafter, embodiments that specifically disclose an endoscope and a method for producing the endoscope according to the present disclosure will be described in detail with reference to the accompanying drawings. However, unnecessarily detailed description may be omitted. For example, detailed description of already well-known matters and redundant description of substantially the same configuration may be omitted. This is to avoid unnecessary redundancy of the following description and facilitate understanding of a person skilled in the art. The accompanying drawings and the following description are provided for a person skilled in the art to sufficiently understand the present disclosure, and are not intended to limit the subject matter described in the claims.

Embodiment 1

Figure 1:
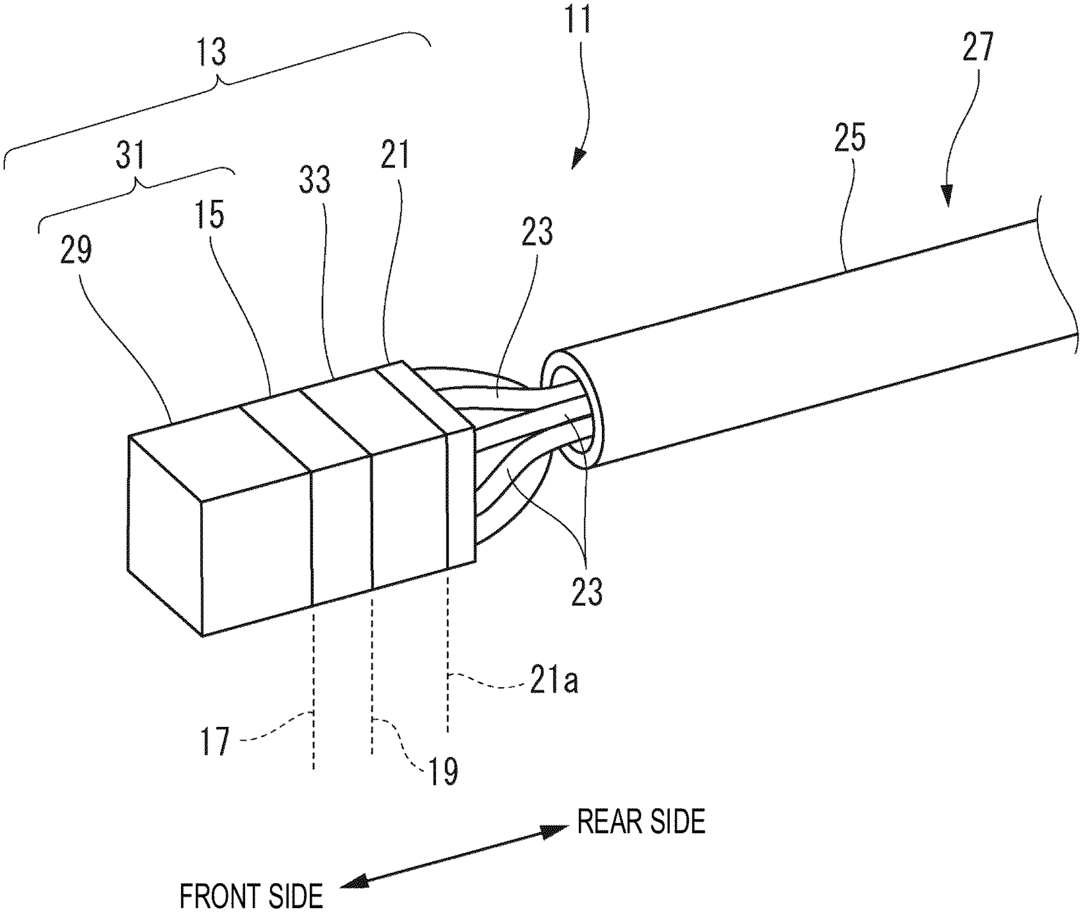
FIG. 1 is a perspective view of a main part of a camera accommodated in a distal end portion of an endoscope according to Embodiment 1.

FIG. 1 is a perspective view of a main part of a camera unit 13 to be accommodated in a distal end portion of an endoscope 11 according to the present embodiment. The endoscope 11 according to the present embodiment accommodates the camera unit 13 in the distal end portion thereof (not shown). The camera unit 13 includes a lens 15 that is a hexahedron, that is, a quadrangular prism, with each surface having quadrangular outer shape. The lens 15 has a first surface 17 having a quadrangular outer shape and a second surface 19 parallel to the first surface 17 and having a quadrangular outer shape. The first surface 17 is an incident surface of the lens 15 onto which imaging light is incident, and the second surface 19 is a back surface of the lens 15. An image sensor 21 is disposed on a back surface side of the lens 15 in the camera unit 13. A transmission cable 27 in which a plurality of electric wires 23 are bundled by a sheath 25 is connected to a back surface of the image sensor 21.

The image sensor 21 has an imaging surface 21*a* onto which imaging light is incident, and is formed in a quadrangular shape having a side length of, for example, 0.5 mm or less. Accordingly, the endoscope 11 can be produced as a so-called submillimeter camera having an outermost diameter of less than 1 mm.

The endoscope 11 is formed to have a small diameter (for example, a small diameter having a submillimeter order). With such a configuration, the endoscope 11 can be inserted into a small-diameter body cavity. That is, the endoscope 11 corresponds to a flexible endoscope for medical use. The small-diameter body cavity is not limited to a blood vessel of a human body, and includes, for example, a ureter, a pancreatic duct, a bile duct, and a bronchiole. That is, the endoscope 11 can be inserted into a blood vessel, a ureter, a pancreatic duct, a bile duct, a bronchiole, or the like of a human body. In other words, the endoscope 11 can be used to observe a lesion in the blood vessel. The endoscope 11 is effective in identifying an atherosclerotic plaque. The endoscope 11 is also applicable to observation during cardiac catheterization. Further, the endoscope 11 is also effective in detecting a blood clot and an atherosclerotic yellow plaque.

In the present disclosure, a front side of the endoscope 11 refers to a side facing an imaging subject. A rear side (back side) of the endoscope 11 refers to a side opposite to the imaging subject with the front side of the endoscope 11 interposed therebetween.

The endoscope 11 includes the camera unit 13 accommodated in the hard distal end portion thereof and the transmission cable 27. The camera unit 13 includes a lens unit 31 and the image sensor 21. The camera unit 13 may include an element cover glass 33 between the lens unit 31 and the image sensor 21. The distal end portion of the endoscope 11 is covered with, for example, a metal tube or a resin mold portion (not shown). With such a configuration, the distal end portion of the endoscope 11 is formed so as not to bend or not to easily bend. In the endoscope 11, a flexible portion (not shown) that bends more easily than the distal end portion extends behind the distal end portion. The transmission cable 27 is mainly inserted into the flexible portion. An insertion portion (not shown) of the endoscope 11 includes the distal end portion and the flexible portion. A plug portion (not shown) connected to a video processor (not shown) of an endoscope system (not shown) is attached to a rear end of the insertion portion of the endoscope 11. The endoscope 11 transmits power and various signals (video signals, control signals, and the like) to and receives power and various signals (video signals, control signals, and the like) from the video processor via the transmission cable 27 and the plug unit.

Figure 2:
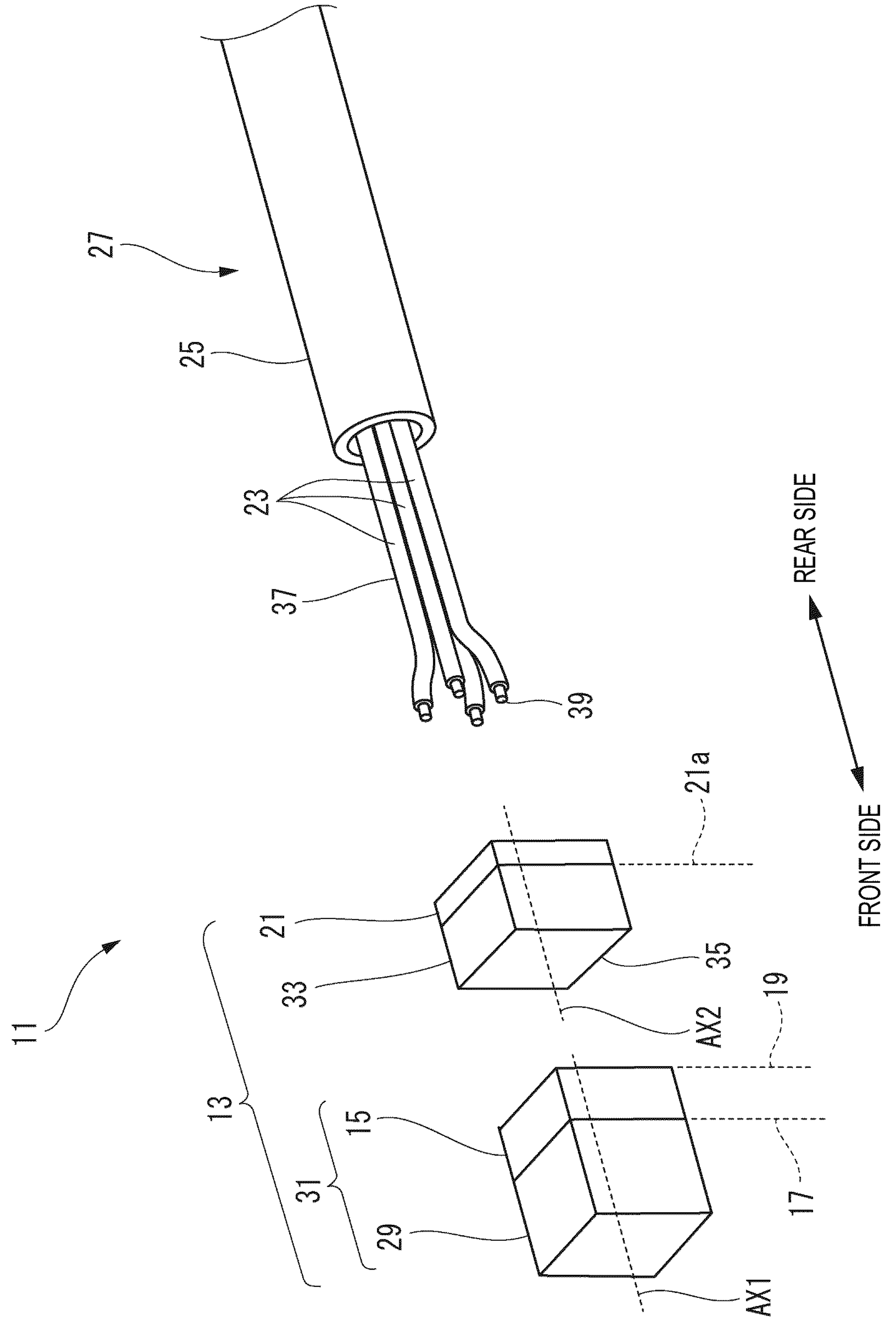
FIG. 2 is an exploded perspective view of the endoscope according to Embodiment 1.

FIG. 2 is an exploded perspective view of the endoscope 11. The lens unit 31 includes an objective cover glass 29 and the lens 15. The objective cover glass 29 is adhesively fixed to a front surface (that is, the first surface 17) of the lens 15. Imaging light from the imaging subject is incident onto the objective cover glass 29. An aperture (not shown) may be provided between the objective cover glass 29 and the lens 15. The endoscope 11 may be formed by joining only the lens 15 to the image sensor 21 without providing the objective cover glass 29 and the aperture.

On the other hand, the element cover glass 33 is integrally adhesively fixed to a front surface of the image sensor 21 (that is, a surface facing the second surface 19: the imaging surface 21*a* of the image sensor 21). The image sensor 21, which is, for example, a square having a small thickness of 0.5 mm, is adhesively fixed to the element cover glass 33 integrally, whereby distortion such as warping can be prevented and handleability (handling) can be improved. A front surface (that is, a surface facing the second surface 19) of the element cover glass 33 corresponds to an adhered surface 35 to be adhesively fixed to the lens 15. The adhered surface 35 has a quadrangular shape having substantially the same size as the lens 15. The endoscope 11 is assembled in a hexahedral shape (see FIG. 1) in which the objective cover glass 29, the aperture, the lens 15, the element cover glass 33, and the image sensor 21 are joined at quadrangular joining surfaces. When the camera unit 13 does not include the element cover glass 33, the imaging surface 21*a* corresponds to the adhered surface. The imaging surface 21*a* and the adhered surface 35 are formed in quadrangular shapes having substantially the same size as the second surface 19 of the lens 15, for example.

The transmission cable 27 is connected to the back surface of the image sensor 21 before or after the image sensor 21 is joined to the lens 15. The transmission cable 27 includes, for example, four electric wires 23 bundled by the sheath 25. Each of the electric wires 23 includes an insulating coating 37 and a conductor 39 covered with the insulating coating 37. The conductor 39 is exposed from the insulating coating 37 at a terminal end of the electric wire 23 by peeling off the insulating coating 37. The image sensor 21 is connected to the transmission cable 27 by connecting distal ends of the conductor 39 to four conductor connection portions (not shown) provided on the back surface of the image sensor 21 by soldering or the like.

Figure 3:
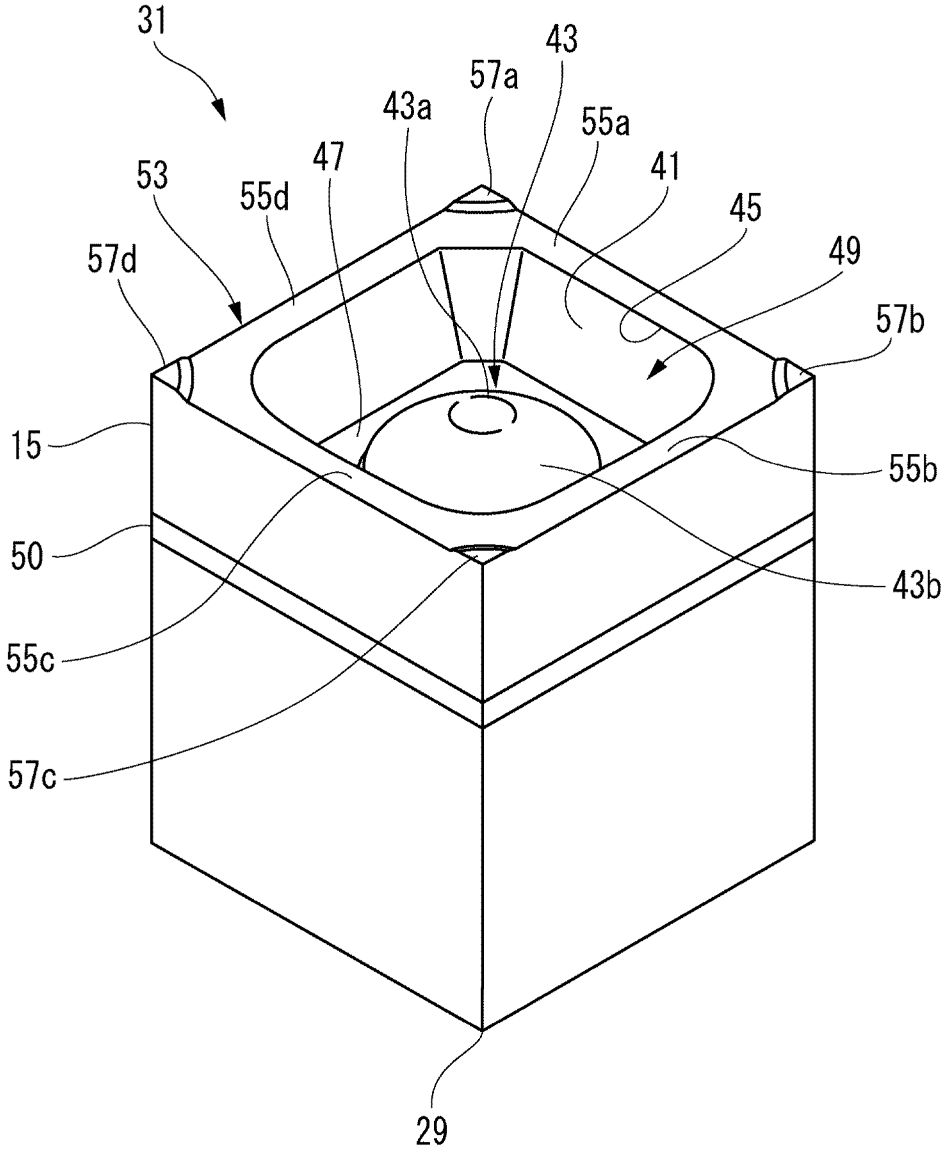
FIG. 3 is an upper perspective view of a lens unit according to Embodiment 1.

FIG. 3 is an upper perspective view of the lens unit 31 when the lens 15 is disposed on an upper side thereof. The lens 15 includes a recess 41, an emission portion 43, and a frame portion 53. The recess 41 has an opening 45, a bottom surface 47, and a in-lens space 49. The opening 45 is formed in the second surface 19 and has a quadrangular shape substantially similar to the outer shape of the second surface 19. The in-lens space 49 corresponds to an inverted truncated pyramidal space, in the recess 41, extending from the opening 45 to the bottom surface 47 while gradually reducing an opening area. In the recess 41, the second surface 19 (see FIG. 1) is recessed toward a front surface side, that is, the second surface 19 is recessed from the back surface of the lens 15 toward the incident surface. That is, the recess 41 is recessed from the opening 45 toward the second surface 19. The bottom surface 47 is parallel to the second surface 19 of the lens 15. The emission portion 43 includes a top portion 43*a* and a convex curved surface portion 43*b*. The convex curved surface portion 43*b* protrudes from the bottom surface 47 toward the second surface 19, that is, from the bottom surface 47 toward the back surface of the lens 15. The convex curved surface portion 43*b* protrudes, in a direction from the bottom surface 47 toward the second surface 19, by a height from the bottom surface 47, that is, a height from the bottom surface 47 to the top portion 43*a* being smaller than that of the second surface 19. The convex curved surface portion 43*b* as an example of an effective curved surface portion of the lens 15 is, for example, a part of a spherical surface, refracts light (that is, imaging light from the imaging subject) transmitted through the objective cover glass 29 and the aperture (not shown), and emits the refracted light to the imaging surface (not shown) of the image sensor 21. In this way, the emission portion 43 emits light at a position between the bottom surface 47 and the second surface 19 in the in-lens space 49, that is, in the direction from the bottom surface 47 toward the second surface 19 (see FIG. 5). The convex curved surface portion 43*b* may be an aspherical surface. The lens 15 is adhesively fixed to the objective cover glass 29 via an adhesive 50 on a front surface (that is, the first surface 17) located on a side opposite to the emission portion 43.

Figure 4:
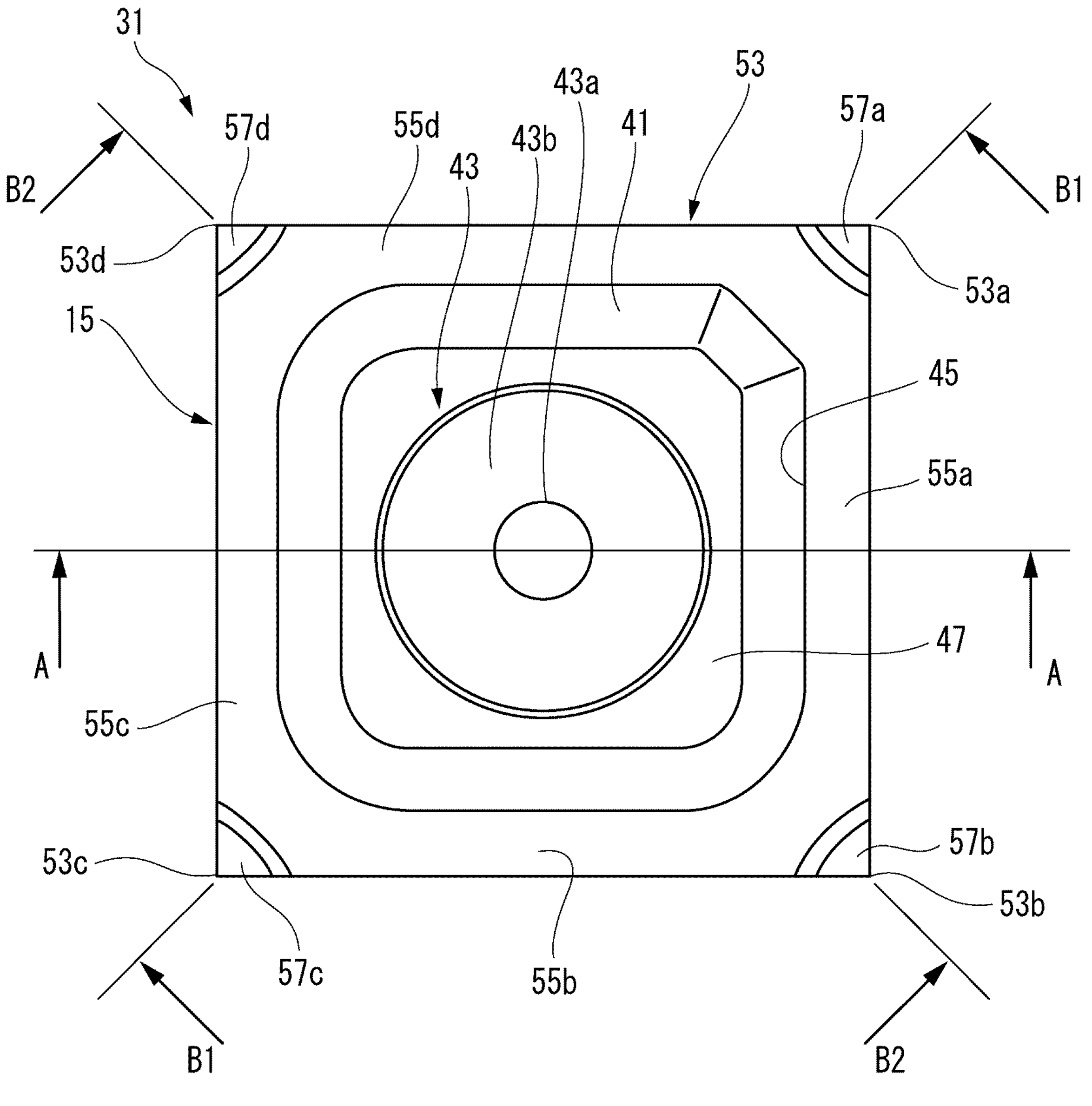
FIG. 4 is a plan view of the lens unit according to Embodiment 1.

FIG. 4 is a top view of the lens unit 31. In the emission portion 43, a line segment passing through the top portion 43*a* and a center of a spherical surface of the convex curved surface portion 43*b* passes through an intersection of a pair of diagonal lines (a diagonal line B1 and a diagonal line B2) of the second surface 19 (see FIG. 1). The emission portion 43 emits the imaging light from the imaging subject, which is incident onto a front surface of the objective cover glass 29, toward the image sensor 21. The imaging light emitted from the emission portion 43 is imaged on the imaging surface 21*a* (see FIGS. 1 and 2) of the image sensor 21. The lens 15 includes the frame portion 53. The frame portion 53 corresponds to a portion of the second surface 19 surrounding the recess 41, and is formed as a frame-shaped end surface extending on the same plane as the second surface 19, for example. The frame portion 53 is a frame in which linear frame portions 55*a*, 55*b*, 55*c*, and 55*d* arranged along sides of the quadrangular shape, a first corner 53*a*, a second corner 53*b*, a third corner 53*c*, and a fourth corner 53*d* are connected into a quadrangular annular shape. The frame portion 53 is fixed to the imaging surface 21*a* of the image sensor 21 (or the adhered surface 35 of the element cover glass 33) via an adhesive 51 (see FIG. 12). In the following description, when it is not necessary to distinguish the linear frame portions 55*a*, 55*b*, 55*c*, 55*d*, . . . , these may be simply referred to as "linear frame portions 55".

The frame portion 53 is provided with protrusions 57*a*, 57*b*, 57*c*, and 57*d*. The protrusions 57*a*, 57*b*, 57*c*, and 57*d* are an example of a protrusion portion according to the present embodiment. Since the protrusions 57*a*, 57*b*, 57*c*, and 57*d* protrude from the frame portion 53 in an optical axis direction X1 (see FIG. 2) of the lens 15 by a height h (see FIG. 7) and abut on the image sensor 21, the frame portion 53 is parallel to the adhered surface 35 or the imaging surface 21*a*. In this way, since the protrusions 57*a*, 57*b*, 57*c*, and 57*d* have the same height h, it is easy to position the lens 15 in parallel to the image sensor 21. In the present embodiment, the protrusions 57*a*, 57*b*, 57*c*, and 57*d* are provided at four corners of the frame portion 53, in other words, four corners of the second surface 19. The protrusions 57*a*, 57*b*, 57*c*, and 57*d* may be integrally molded with the lens 15.

The protrusions 57*a*, 57*b*, 57*c*, and 57*d* have the height h and are formed at the four corners of the frame portion 53 having a quadrangular outer shape. Therefore, the lens 15 and the image sensor 21 can be stably positioned in parallel by abutting the lens 15 on the imaging surface 21*a* (or the adhered surface 35).

Specifically, the protrusion 57*a* is formed at the first corner 53*a* of the frame portion 53. The first corner 53*a* corresponds to a location intersecting the diagonal line B1, among the four corners of the frame portion 53. The protrusion 57*b* is formed at the second corner 53*b* of the frame portion 53. The protrusion 57*c* is formed at the second corner 53*c* of the frame portion 53. The second corner 53*c* corresponds to a location intersecting the diagonal line B1 and different from the first corner 53*a*, among the four corners of the frame portion 53. The third corner 53*b* corresponds to a location intersecting the diagonal line B2 that intersects the diagonal line B1, among the four corners of the frame portion 53. The protrusion 57*d* is formed at the fourth corner 53*d* of the frame portion 53. The fourth corner 53*d* corresponds to a location intersecting the diagonal line B2 and different from the third corner 53*b*, among the four corners of the frame portion 53. The protrusion 57*a* corresponds to a first protrusion according to the present embodiment, and the protrusion 57*c* corresponds to a second protrusion according to the present embodiment. The protrusion 57*b* corresponds to a third protrusion according to the present embodiment, and the protrusion 57*d* corresponds to a fourth protrusion according to the present embodiment.

Positions of the protrusions 57*a*, 57*b*, 57*c*, and 57*d* are not limited thereto. Each of the four corners of the frame portion 53 includes an outer corner and an inner corner. The four corners have a larger area than the linear frame portions 55*a*, 55*b*, 55*c*, and 55*d*. The outer corner is a portion where outer sides of the frame portion 53 are orthogonal. The inner corner is a portion where inner sides of the frame portion 53 intersect.

The protrusion 57*a* may be provided over the entire line connecting an outer corner of the first corner 53*a* and an inner corner of the first corner 53*a*. The protrusion 57*a* may be provided in a part of the line connecting the outer corner of the first corner 53*a* and the inner corner of the first corner 53*a*. In this way, the first corner 53*a* larger than the linear frame portion 55*a* can be effectively used by providing the protrusion 57*a* in a part of the first corner 53*a* on an outer corner side. For example, it is possible to apply the adhesive 51 to the frame portion 53 in a continuous annular shape having a constant width and without interruption. By applying the adhesive 51 in the continuous annular shape without interruption, it is possible to prevent leakage of reflected light from the recess 41 and to prevent stray light. Similarly to the protrusion 57*a*, each of the protrusions 57*b*, 57*c*, and 57*d* may be formed over the entire line connecting an outer corner and an inner corner of the frame portion 53, or may be formed in a part of the line connecting the outer corner and the inner corner of the frame portion 53.

The endoscope 11 according to the present embodiment includes the protrusions 57*a*, 57*b*, 57*c*, and 57*d* each having a quarter-circular shape in a plan view, that is, in a direction from the second surface 19 toward the first surface 17, that is, a fan shape. The protrusions 57*a*, 57*b*, 57*c*, and 57*d* are formed in the frame portion 53 each in the fan shape centered on the outer corner in a part of an outer corner side on the line connecting the corner and the inner corner. The direction from the second surface 19 toward the first surface 17 on an optical axis AX1 (see FIG. 2) of the lens 15 corresponds to a first direction according to the present embodiment.

Figure 5:
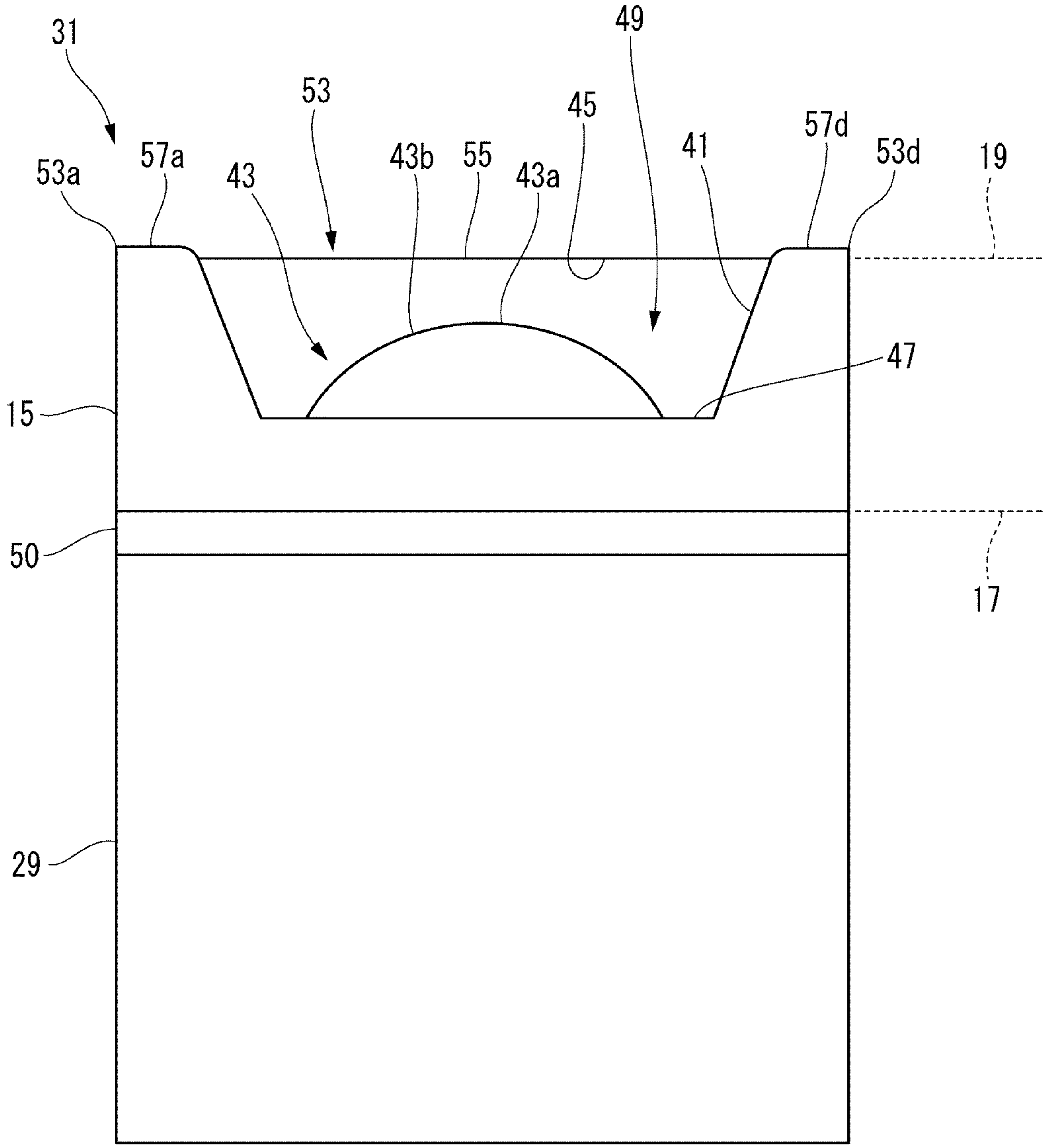
FIG. 5 is a cross-sectional view of the lens unit according to Embodiment 1 taken along a line A-A.

FIG. 5 is a cross-sectional view of the lens 15 according to the present embodiment. FIG. 5 shows a cross section of the lens 15 taken along a line A-A (see FIG. 4). The lens 15 is fixed to the image sensor 21 via the adhesive 51 in a state in which the protrusions 57*a*, 57*b*, 57*c*, and 57*d* (the protrusions 57*c* and 57*b* are not shown in FIG. 5) abut on the adhered surface 35 or the imaging surface 21*a* (see FIG. 2). Therefore, the adhesive 51 adhesively fixes the frame portion 53 to the adhered surface 35 or the imaging surface 21*a* between the protrusions. In the present embodiment, the adhesive 51 adhesively fixes the adhered surface 35 or the imaging surface 21*a* to an inner corner side on the lines connecting the outer corner and the inner corner at each of the four corners of the frame portion 53. At least a part of each of the protrusions 57*a*, 57*b*, 57*c*, and 57*d* is embedded in the adhesive 51. In Embodiment 1, for example, each of the protrusions 57*a*, 57*b*, 57*c*, and 57*d* has a quarter-circular arc portion embedded in the adhesive 51.

The lens unit 31 can be produced by bonding together the objective cover glass 29 having a large area, an aperture array in which a plurality of openings are formed vertically and horizontally, and a lens array in which a plurality of recesses 41 and emission portions 43 are formed vertically and horizontally, and cutting (dicing) these into lens units (small pieces). At this time, the lens array is adhesively fixed to the objective cover glass 29 when no aperture array or aperture is used. In this case, by providing protrusions on a front surface of the lens array, the lens unit 31 can also quantify an adhesion thickness by making an adhesion gap between the lens array and the aperture array or between the lens array and the objective cover glass 29 constant.

In the lens 15, the quarter-circular protrusions 57*a*, 57*b*, 57*c*, and 57*d* provided at the four corners of the frame portion 53 described above are each formed into the quarter-circular shape by dicing circular protrusions vertically and horizontally through centers of the circular protrusions, and the circular protrusions are on a lens array surface formed in all directions surrounding the emission portions 43 before being divided into small pieces (dicing).

Figure 6:
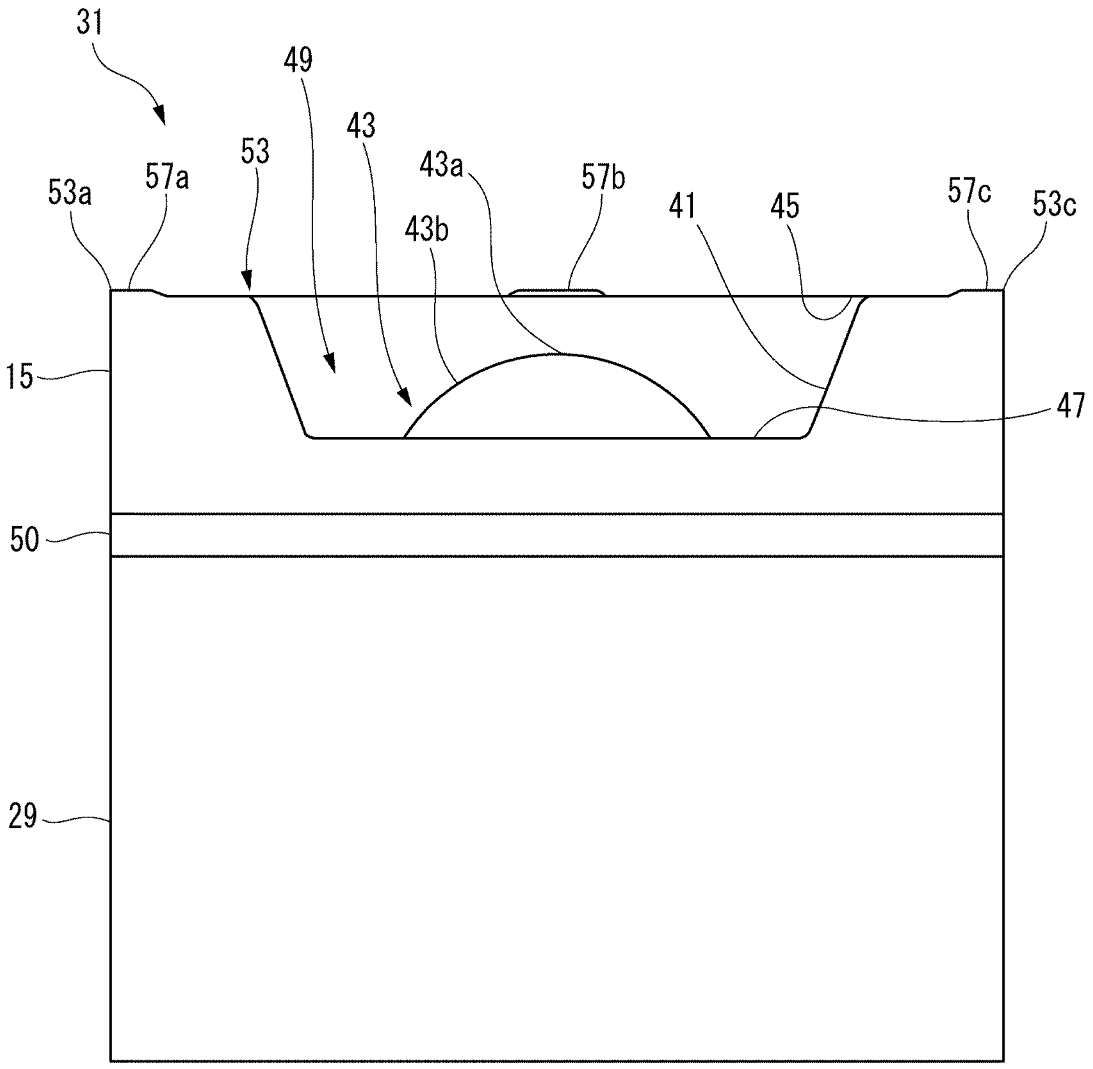
FIG. 6 is a cross-sectional view of the lens unit according to Embodiment 1 taken along a line B-B.

FIG. 6 is a cross-sectional view of the lens 15 according to the present embodiment. FIG. 6 shows a cross section of the lens 15 taken along a line B1-B1 (see FIG. 4). The protrusions 57*a*, 57*b*, 57*c*, and 57*d* (the protrusions 57*b* and 57*d* are not shown in FIG. 6) protrude from the frame portion 53 by the height h (see FIG. 7). Since the protrusions 57*a*, 57*b*, 57*c*, and 57*d* protrude from the frame portion 53 at the same height h, the protrusions 57*a*, 57*b*, 57*c*, and 57*d* abut on the front surface (that is, the imaging surface 21*a*) of the image sensor 21 or the adhered surface 35. With such a configuration, in the endoscope 11, the second surface 19 of the lens 15 and the imaging surface 21*a* of the image sensor 21 or the adhered surface 35 can be positioned in parallel with highly accurate flatness. Accordingly, between the frame portion 53 and the imaging surface 21*a* of the image sensor 21 or the adhered surface 35, a uniform gap corresponding to the height h of the protrusions 57*a*, 57*b*, 57*c*, and 57*d* is formed in a peripheral direction of the frame portion 53, that is, around the opening 45 in the frame portion 53. When the gap between the frame portion 53 and the imaging surface 21*a* of the image sensor 21 or the adhered surface 35 is filled with the adhesive 51, the lens 15 is adhesively fixed to the image sensor 21 in the endoscope 11.

In the endoscope 11, the lens 15 is adhered to the image sensor 21 with a thickness corresponding to the height h of the protrusion 57. This makes it extremely easy to manage the adhesion thickness between the lens 15 and the image sensor 21 in the present embodiment. Therefore, in the endoscope 11, since a stable adhesive force can be ensured between the lens 15 and the image sensor 21, and the lens 15 is less likely to be warped, deterioration in image quality (unstableness in image quality) due to variations in adhesion thickness can be prevented.

Figure 7:
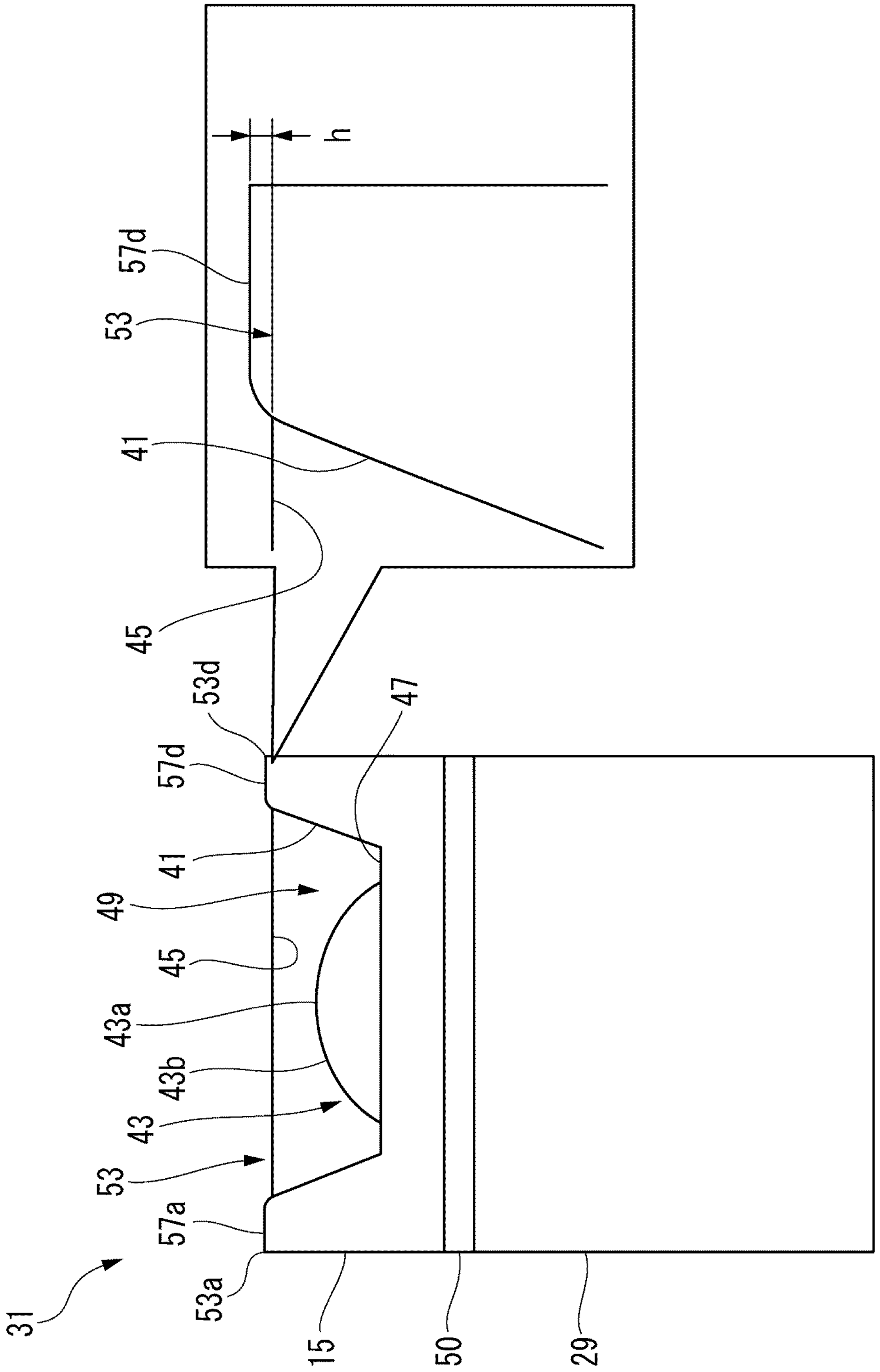
FIG. 7 is an explanatory diagram showing an A-A cross section of the lens unit according to Embodiment 1 together with an enlarged view of a main part thereof.

FIG. 7 is an explanatory diagram showing the A-A cross section (see FIG. 4) of the lens 15 according to the present embodiment and an enlarged view of a main part of the lens 15. In the present embodiment, since the protrusions 57*a*, 57*b*, 57*c*, and 57*d* have a common configuration except for arrangement positions in the frame portion 53, the protrusion 57*d* will be described as an example.

The height h of the protrusion 57*d* can be set to, for example, 0.001 mm to 0.005 mm. A lower limit value 0.001 mm of the height h of the protrusion 57*d* means that the protrusion 57*d* is always present in the lens 15. The adhesive 51 is applied to the frame portion 53 having the protrusion 57*d* with a thickness of, for example, 0.020 mm to 0.050 mm. In the present embodiment, in order to prevent an optical effective area Oa (see FIG. 11C) of the endoscope 11 from being contaminated with the adhesive 51, an upper limit is set for an application thickness of the adhesive 51. In the present embodiment, the upper limit of the application thickness of the adhesive 51 is, for example, 0.050 mm.

A plurality of types of lenses 15 in which the height h of the protrusions 57*a*, 57*b*, 57*c*, and 57*d* is changed may be produced. By changing the height h of the protrusions 57*a*, 57*b*, 57*c*, and 57*d*, the lens 15 can be used with different specifications of a back focus. That is, the endoscope 11 can obtain different viewing depths by changing only the height h of the protrusions 57*a*, 57*b*, 57*c*, and 57*d*. By changing the height h of the protrusions 57*a*, 57*b*, 57*c*, and 57*d*, it is possible to easily arrange a lineup of the endoscope 11 for a plurality of purposes (for example, for gastroenterology, respiratory, intravascular plaque identification, and intravascular path visualization).

Figure 8A:
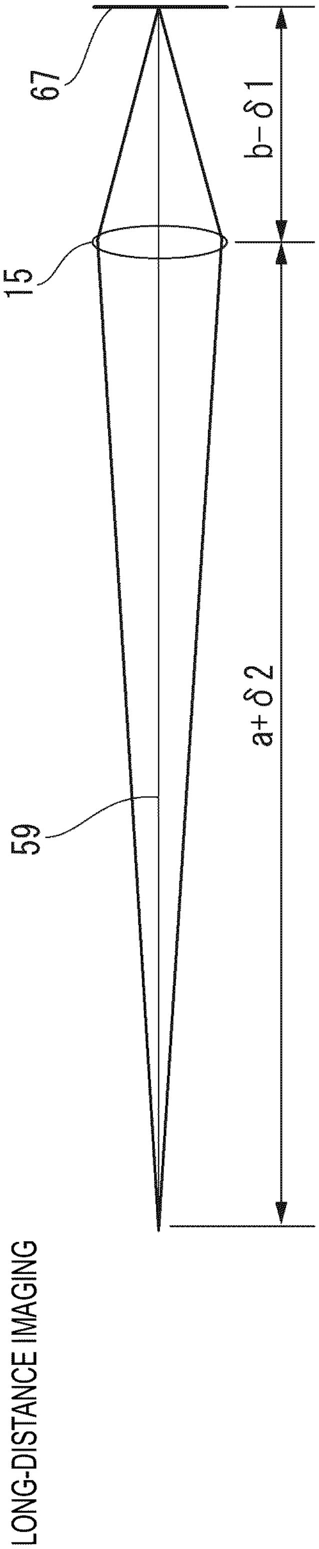
FIG. 8A is a schematic diagram showing a relationship between a protrusion height and a back focus.
Figure 8B:
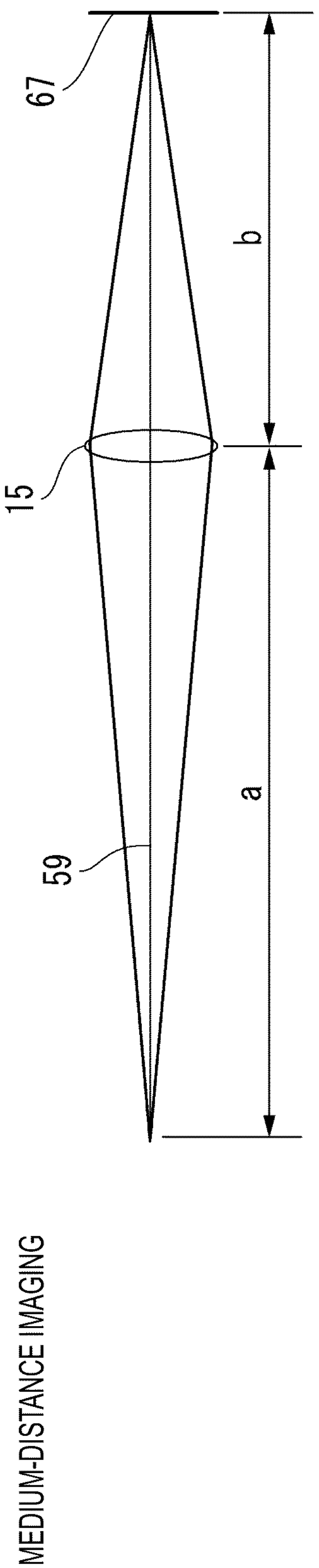
FIG. 8B is a schematic diagram showing a relationship between a protrusion height and a back focus.
Figure 8C:
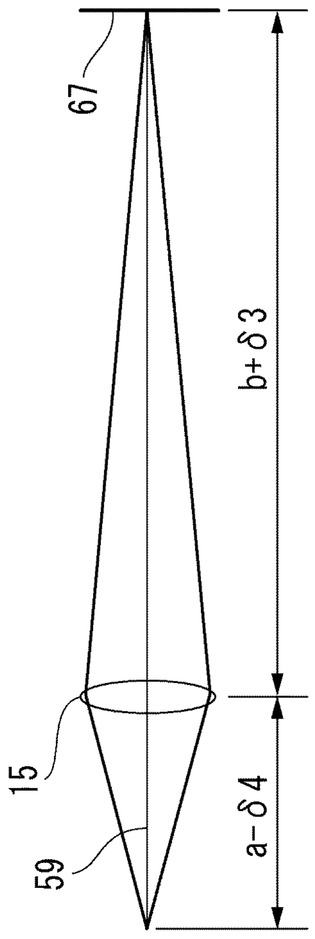
FIG. 8C is a schematic diagram showing a relationship between a protrusion height and a back focus.

Specifically, a back focus of the endoscope 11 can be set by abutting the protrusions 57*a*, 57*b*, 57*c*, and 57*d* on the image sensor 21. Since the protrusions 57*a*, 57*b*, 57*c*, and 57*d* protrude from the frame portion 53 by the height h, a distance to an imaging subject side that is most in focus (imaging distance) changes depending on the height h of the protrusions 57*a*, 57*b*, 57*c*, and 57*d*. FIGS. 8A, 8B, and 8C are schematic diagrams each showing a relationship between the height h of the protrusions 57*a*, 57*b*, 57*c*, and 57*d* and the back focus of the lens 15. In the following description, when it is not necessary to distinguish the protrusions 57*a*, 57*b*, 57*c*, and 57*d*, these may be simply referred to as "protrusions 57".

Here, as shown in FIG. 8B, it is assumed that a distance from the imaging subject to the lens 15 (strictly a front principal point) is a and a distance from the lens 15 (strictly a rear principal point) to an image plane 67 is b. In this case, when a front focal point f and a rear focal point f of the lens 15 are the same, a lens imaging equation ($1/a+1/b=1/f$) is satisfied. The image plane 67 corresponds to, for example, the imaging surface 21*a*.

Therefore, as shown in FIG. 8A, as a distance b to the image plane 67 decreases ($b-\delta 1$), a distance a to the imaging subject increases ($a+\delta 2$). That is, when a back focus distance of the lens 15 is small (the height h of the protrusions 57 is small), a distance to the imaging subject that the lens 15 focuses on becomes large. As shown in FIG. 8C, as the distance b to the image plane 67 increases ($b+\delta 3$), the distance a to the imaging subject decreases ($a-\delta 4$). That is, when a back focus distance of the lens 15 is large (the height h of the protrusions 57 is large), a distance to the imaging subject that the lens 15 focuses on becomes small. In addition, $\delta 1$, $\delta 2$, $\delta 3$, and $\delta 4$ are positive numbers.

As a result, in Embodiment 1, by changing only the height h of the protrusions 57, the imaging distance is changed, thereby easily achieving the lineup of the endoscope 11 for a long-distance imaging purpose, a medium-distance imaging purpose, and a short-distance imaging purpose (for example, for gastroenterology, respiratory, intravascular plaque identification, and intravascular path visualization).

Further, by arranging other types of lenses 15 (for example, emission portions including convex curved surface portions having different curvatures), it is possible to further enrich the type of the lens 15 and the type of the back focus of the lens 15, and further increase the product lineup of the endoscope 11.

Figure 9:
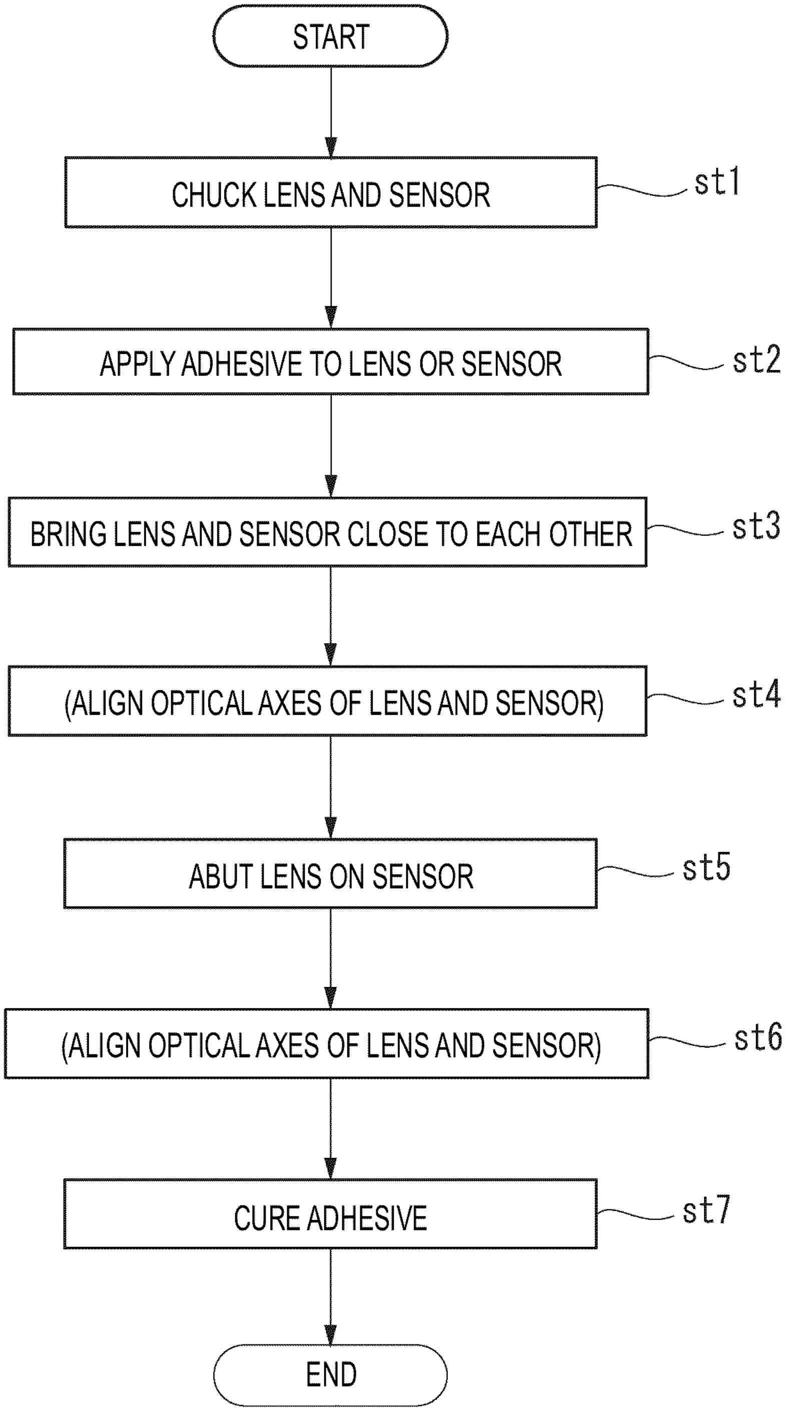
FIG. 9 is a flowchart showing a procedure of a method for producing the endoscope.

Next, a method for producing the endoscope 11 will be described. FIG. 9 is a flowchart showing a procedure of the method for producing the endoscope 11 according to Embodiment 1. FIGS. 10A, 10B, 10C, 10D, 10E, and 10F are explanatory diagrams showing states of the lens 15 and the image sensor 21 in a production process of the endoscope 11.

In the method for producing the endoscope according to Embodiment 1, the lens 15 having the recess 41 in the second surface 19 is used. The emission portion 43 is formed in the recess 41. The emission portion 43 includes the convex curved surface portion 43*b* protruding from the bottom surface 47. The frame portion 53 surrounding the recess 41 is provided with the protrusions 57 (for example, protrusions 57*a*, 57*b*, 57*c*, and 57*d*).

Figure 10A:
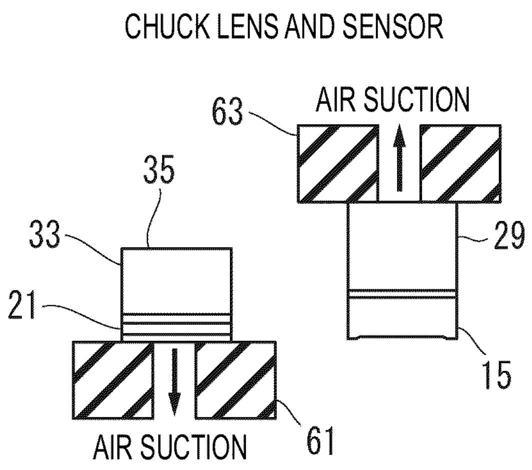
FIG. 10A is an explanatory diagram showing a state of a lens and an image sensor.

In the method for producing the endoscope, first, in a holding step, the lens 15 and the image sensor 21 are each chucked (st1). As shown in FIG. 10A, in the holding step (st1), the image sensor 21 is held by air suction by a sensor chuck 61, and the lens unit 31 is held by air suction by a lens chuck 63. The image sensor 21 is sucked on a surface opposite to the adhered surface 35 (or the imaging surface 21*a*). In the lens unit 31, the front surface of the objective cover glass 29 is sucked.

Figure 10B:
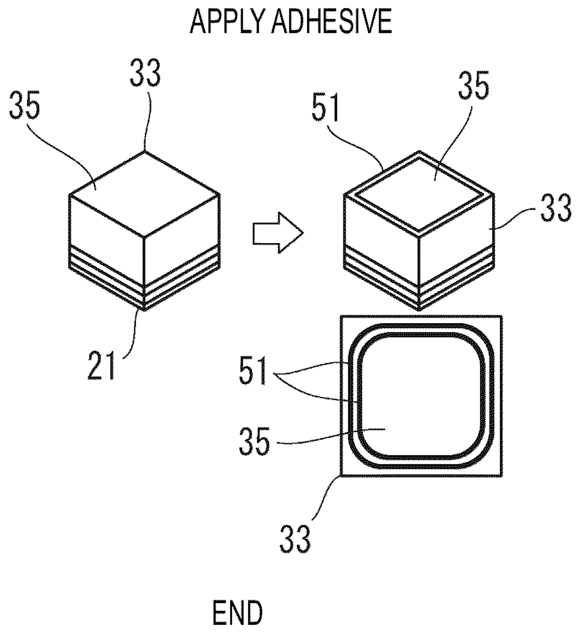
FIG. 10B is an explanatory diagram showing a state of the lens and the image sensor.

Subsequently, in the method for producing the endoscope, in an application step, the adhesive 51 is applied to any one of the imaging surface 21*a* of the image sensor 21 or the adhered surface 35 and the frame portion 53 of the lens 15 (st2). As shown in FIG. 10B, in the application step (st2), for example, the adhesive 51 is applied in a quadrangular frame shape to the front surface (that is, the adhered surface 35) of the element cover glass 33. In the application step, the adhesive 51 is applied with a predetermined thickness (height) within a range not protruding from a projection region of the frame portion 53. At this time, the lens unit 31 is turned upside down to prevent the adhesive 51 from dripping due to gravity. The adhesive 51 is applied within a range corresponding to the inside of the frame portion 53 of the lens 15. The adhesive 51 can be applied in a single frame shape or a double frame shape in a substantially quadrangular shape. As the adhesive 51, for example, an ultraviolet curable adhesive 51 is used. In the present embodiment, the substantially quadrangular shape corresponds to a shape in which each corner of a quadrangular frame is chamfered.

Figure 10C:
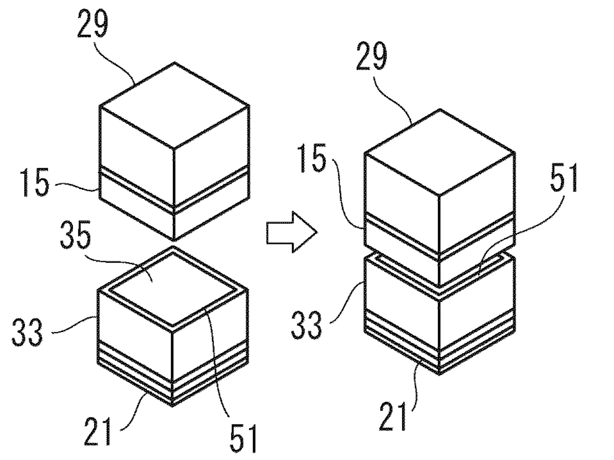
FIG. 10C is an explanatory diagram showing a state of the lens and the image sensor.

Subsequently, in the method for producing the endoscope, an approaching step (st3) is performed in which the lens 15 and the image sensor 21 are brought close to each other. As shown in FIG. 10C, in the approaching step (st3), for example, the sensor chuck 61 and the lens chuck 63 are moved by an actuator (not shown), and the image sensor 21 and the lens unit 31 are brought close to each other such that the frame portion 53 and the adhered surface 35 (or the imaging surface 21*a*) come close to each other. The movement is preferably a relative movement in which the image sensor 21 applied with the adhesive 51 is fixed and the lens unit 31 with the frame portion 53 facing downward is processed from above.

Figure 10D:
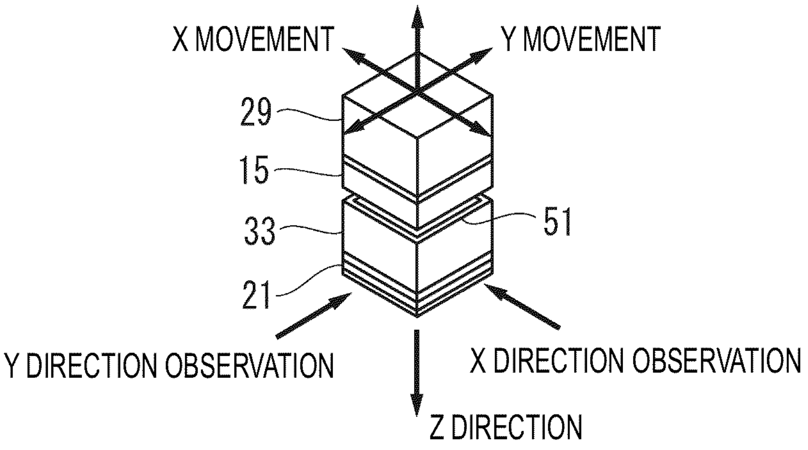
FIG. 10D is an explanatory diagram showing a state of the lens and the image sensor.

In the method for producing the endoscope, after the approaching step (st3) is performed, in an optical axis alignment step, the optical axis AX1 of the lens 15 (see FIG. 2) and an optical axis AX2 of the image sensor 21 (see FIG. 2) are aligned (st4). As shown in FIG. 10D, in the optical axis alignment step (st4), the optical axis AX1 (see FIG. 2) of the lens 15 and the optical axis AX2 (see FIG. 2) of the image sensor 21 are aligned by aligning outer shapes of the lens 15 and the image sensor 21. The second surface 19 of the lens 15 and the adhered surface 35 of the image sensor 21 are formed in the quadrangular shapes of substantially the same size. The optical axis AX1 of the lens 15 is an axis passing through an intersection of a pair of diagonal lines of the second surface 19 in a Z direction perpendicular to the second surface 19 (see FIG. 10D). The optical axis AX2 of the image sensor 21 is an axis passing through an intersection of a pair of diagonal lines of the adhered surface 35 in a direction (Z direction) perpendicular to the adhered surface 35 (or the imaging surface 21*a*).

In the optical axis alignment step, when an axis of the camera unit 13 (see FIG. 1) is defined as an optical axis 59, the lens 15 and the image sensor 21 are moved such that amounts of deviation of the outer shapes of the lens 15 and the image sensor 21 observed from two directions (an X direction and a Y direction) orthogonal to each other through the optical axis 59 are equal in a plane (XY plane) perpendicular to the optical axis 59. In this way, the optical axis AX1 of the lens 15 and the optical axis AX2 of the image sensor 21 indirectly coincide with each other. The optical axis 59 is formed by indirectly making the optical axis AX1 of the lens 15 and the optical axis AX2 of the image sensor 21 to coincide with each other. The camera unit 13 may be rotationally symmetric about the optical axis 59. In this way, since the optical axis AX1 and the optical axis AX2 can be aligned with higher accuracy, it is possible to prevent deviation of the optical axis due to production errors (including tolerances) of the lens 15 and the image sensor 21.

Further, in the optical axis alignment step according to the present embodiment, it is not necessary to align the lens 15 and the image sensor 21 while visually recognizing the captured image output from the image sensor 21. Therefore, since it is not necessary to connect the transmission cable 27 before the lens 15 and the image sensor 21 are joined, it is possible to prevent deterioration in workability due to addition of a cleaning step, addition of equipment, or the like.

Figure 10E:
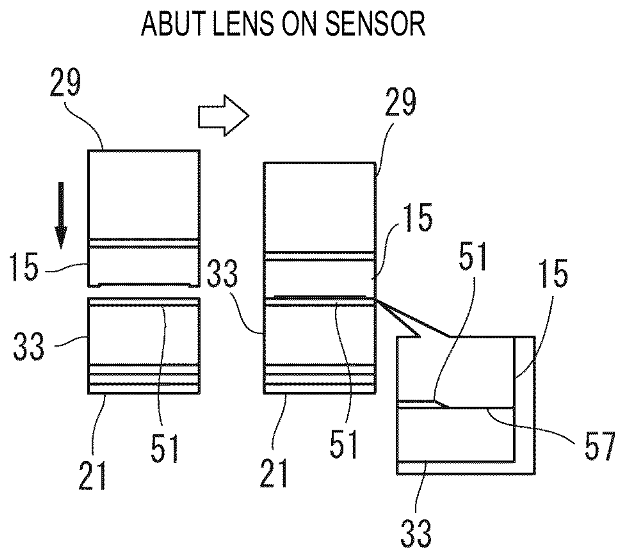
FIG. 10E is an explanatory diagram showing a state of the lens and the image sensor.

Subsequently, in the method for producing the endoscope, the lens 15 abuts on the image sensor 21 via the protrusions 57 in an abutment step (st5). As shown in FIG. 10E, in the abutment step (st5), the frame portion 53 of the lens 15 abuts on the imaging surface 21*a* or the adhered surface 35. Since the protrusions 57 are formed at the frame portion 53, the lens 15 abuts on the image sensor 21 via the protrusions 57 and the imaging surface 21*a* or the adhered surface 35. Accordingly, the adhesive 51 applied to the imaging surface 21*a* or the adhered surface 35 is crushed to approximately the height of the protrusions 57, and is extended to spread over the entire surface of the frame portion 53.

When the lens 15 abuts on the image sensor 21, the plurality of protrusions 57 formed at the frame portion 53 of the lens 15 abut on the adhered surface 35 of the image sensor 21 at the same time. At least a part of the protrusion 57 is embedded in the adhesive 51. The protrusion 57 may be entirely embedded in the adhesive 51.

Figure 11A:
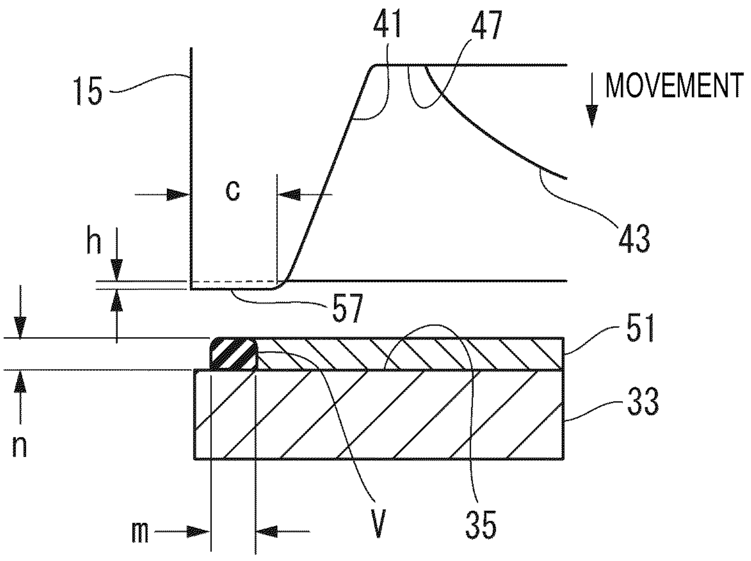
FIG. 11A is an explanatory diagram showing a behavior of an adhesive in an abutment step.
Figure 11B:
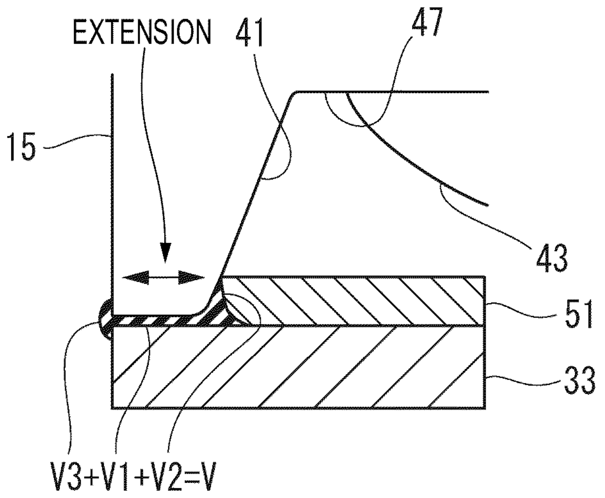
FIG. 11B is an explanatory diagram showing a behavior of the adhesive in the abutment step.
Figure 11C:
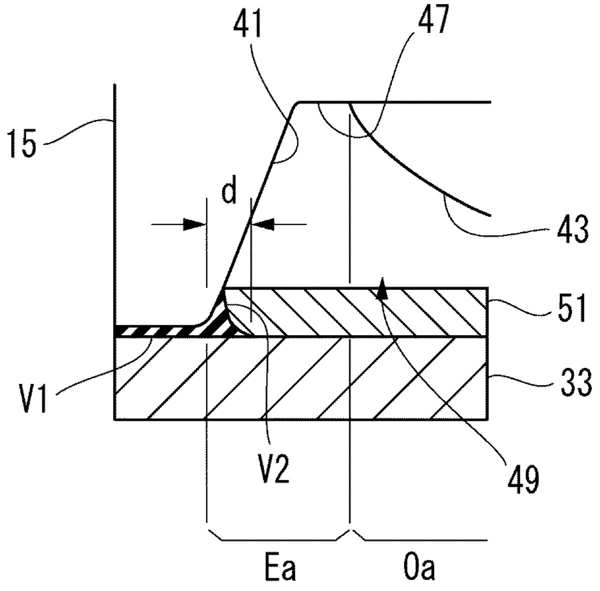
FIG. 11C is an explanatory diagram showing a behavior of the adhesive in the abutment step.

FIGS. 11A, 11B, and 11C are explanatory diagrams showing behaviors of the adhesive 51 in the abutment step. As shown in FIG. 11A, in the application step, the adhesive 51 is applied to be thicker than the height h of the protrusion 57. Here, it is assumed that the adhesive 51 is applied in any cross section orthogonal to a longitudinal direction of the linear end surface 55 with a cross-sectional area having an application width m and an application height n. However, the application width m is smaller than an end surface width c of the linear end surface 55 ($m<c$). The application height n is larger than the height h of the protrusions 57 ($n>h$).

In the abutment step, as the lens 15 and the image sensor 21 approach each other, the adhesive 51 is sandwiched and crushed between the frame portion 53 and the adhered surface 35 (or the imaging surface 21*a*). The adhesive 51 is pushed to spread (that is, extended) in a direction parallel to the frame portion 53 and the adhered surface 35 (or the imaging surface 21*a*) in a state of being in close contact with the frame portion 53 and the adhered surface 35 (or the imaging surface 21*a*).

In the lens 15 and the image sensor 21, the protrusions 57 abut on the adhered surface 35 (or the imaging surface 21*a*), thereby restricting the lens 15 and the image sensor 21 from approaching closer than the height h of the protrusions 57. Therefore, the adhered surface 35 (or the imaging surface 21*a*) is positioned with respect to the entire periphery of the frame portion 53 while maintaining an adhesive thickness corresponding to the height h of the protrusions 57.

In the abutment step, the adhesive 51 is deformed such that a cross-sectional area thereof before the extension includes a recess side flowing portion V2, an end surface joining portion V1, and an outer shape side flowing portion V3. Among these, the outer shape side flowing portion V3 can be removed by trimming before or after a curing step. On the other hand, the recess side flowing portion V2 cannot be removed since the recess 41 becomes a sealed space. Since the cross-sectional area of the adhesive 51 is set to a certain amount or less in advance, the recess side flowing portion V2 protrudes by a distance d and remains in a non-interference region Ea spaced apart from the emission portion 43 of the lens 15. That is, in order to prevent the adhesive 51 from entering an optical effective area Oa or contaminating the optical effective area Oa, an upper limit is set for the thickness of the adhesive 51 (the application width m and the application height n in the cross-sectional area) in the abutment step.

Subsequently, in the method for producing the endoscope, in an optical axis adjustment step, the optical axis AX1 of the lens 15 and the optical axis AX2 of the image sensor 21 are finely adjusted. In the optical axis adjustment step (st6), the lens 15 and the image sensor 21 are finely adjusted again such that the amounts of deviation of the outer shapes of the lens 15 and the image sensor 21 observed from the two directions (the X direction and the Y direction) orthogonal to each other through the optical axis 59 are equal. In this way, the optical axis AX1 of the lens 15 and the optical axis AX2 of the image sensor 21 finally coincide with each other with high accuracy (in other words, the optical axis AX1 and the optical axis AX2 are arranged coaxially with an optical axis AX59). The optical axis adjustment step (st6) may be omitted when there is no deviation of the outer shapes of the lens 15 and the image sensor 21. When the optical axis adjustment step (st6) is preferentially performed, the optical axis alignment step (st4) may be omitted.

Figure 10F:
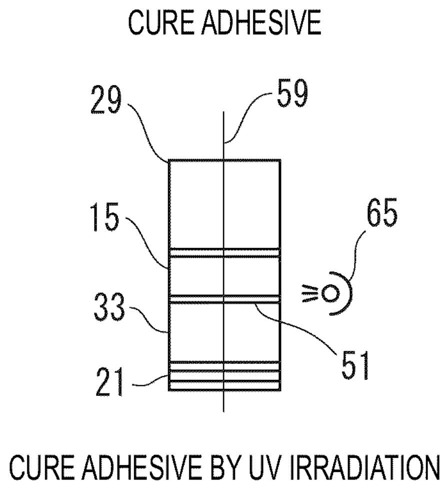
FIG. 10F is an explanatory diagram showing a state of the lens and the image sensor.

Subsequently, in the method for producing the endoscope, in the curing step, the adhesive 51 is cured (st7). As shown in FIG. 10F, in the curing step (st7), the adhesive 51 is cured by UV irradiation. A light source 65 that emits light in a wavelength range in which the ultraviolet curable adhesive 51 is cured is used for the UV irradiation. By the UV irradiation, the lens 15 and the image sensor 21 are fixed to each other with a uniform adhesion thickness between the frame portion 53 and the imaging surface 21*a* or the adhered surface 35, via the solidified adhesive 51 having a thickness of the height h of the protrusions 57. Accordingly, the lens 15 is integrally fixed to the image sensor 21.

In this way, in the endoscope 11, since the lens 15 and the image sensor 21 are solidified with the thickness of the height h of the protrusions 57, the adhesion thickness between the lens 15 and the image sensor 21 can be easily quantified. This makes it extremely easy to manage the adhesion thickness between the lens 15 and the image sensor 21 in the present embodiment. Therefore, in the endoscope 11, since a stable adhesive force can be ensured between the lens 15 and the image sensor 21, and the lens 15 is less likely to be warped, deterioration in image quality (unstableness in image quality) due to variations in adhesion thickness can be prevented.

Modification 1

Figure 12:
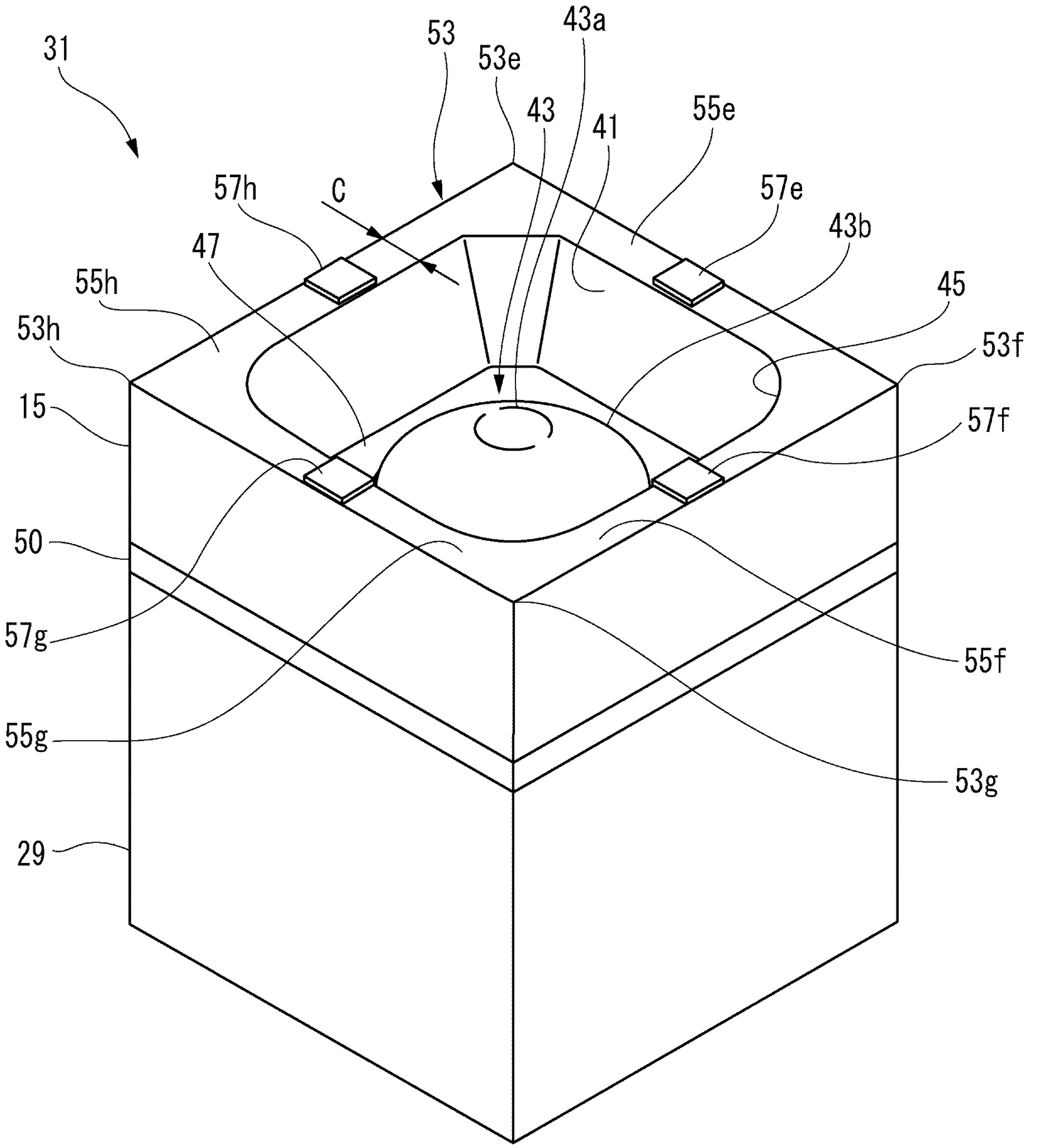
FIG. 12 is a perspective view of a lens according to Modification 1.

As shown in the following modification, protrusions 57*e*, 57*g*, 57*f*, and 57*h* may be formed at the second surface 19 of the lens 15 with different shapes and arrangements. The protrusions 57*e*, 57*g*, 57*f*, and 57*h* are an example of the protrusion portion according to the present modification. FIG. 12 is a perspective view of the lens 15 according to Modification 1. The frame portion 53 according to the present modification includes linear frame portions 55*e*, 55*g*, 55*f*, and 55*h*. The linear frame portion 55*e* corresponds to a linear end surface disposed between a first corner 53*e* and a second corner 53*f* of the frame portion 53. The linear frame portion 55*e* corresponds to a first linear frame portion according to the present modification. The linear frame portion 55*g* corresponds to a linear end surface disposed parallel to the linear frame portion 55*e*. The linear frame portion 55*g* corresponds to a second linear frame portion according to the present modification. The linear frame portion 55*f* corresponds to a linear end surface orthogonal to the linear frame portion 55*e* and the linear frame portion 55*g*. The linear frame portion 55*f* corresponds to a third linear frame portion according to the present modification. The linear frame portion 55*h* corresponds to a linear end surface disposed parallel to the linear frame portion 55*f*. The linear frame portion 55*h* corresponds to a fourth linear frame portion according to the present modification.

The protrusion 57*e* is formed at a central portion of the linear frame portion 55*e*. The protrusion 57*e* corresponds to a first protrusion according to the present modification. The protrusion 57*g* is formed at a central portion of the linear frame portion 55*g*. The protrusion 57*g* corresponds to a second protrusion according to the present modification. The protrusion 57*f* is formed at a central portion of the linear frame portion 55*f*. The protrusion 57*f* corresponds to a third protrusion according to the present modification. The protrusion 57*h* is formed at a central portion of the linear frame portion 55*h*. The protrusion 57*h* corresponds to a fourth protrusion according to the present modification. The protrusion 57*e* may be provided at the central portion of the linear frame portion 55*e* in a longitudinal direction. In this case, the protrusion 57*e* can be formed in a square shape having one side equal to the end surface width c of the linear end surface 55. Each of the protrusions 57*g*, 57*f*, and 57*h* may also be formed in a square shape having one side equal to the end surface width c, similarly to the protrusion 57*e*. The protrusions 57*e*, 57*g*, 57*f*, and 57*h* may be integrally molded with the lens 15.

In this way, the adhesive 51 is applied to four corners of the frame portion 53 by forming the protrusions 57 at central portions of the frame portion 53. In Modification 1, since a joining area between the lens 15 and the image sensor 21 by the adhesive 51 can be increased, an adhesive strength between the lens 15 and the image sensor 21 can be improved.

Modification 2

Figure 13:
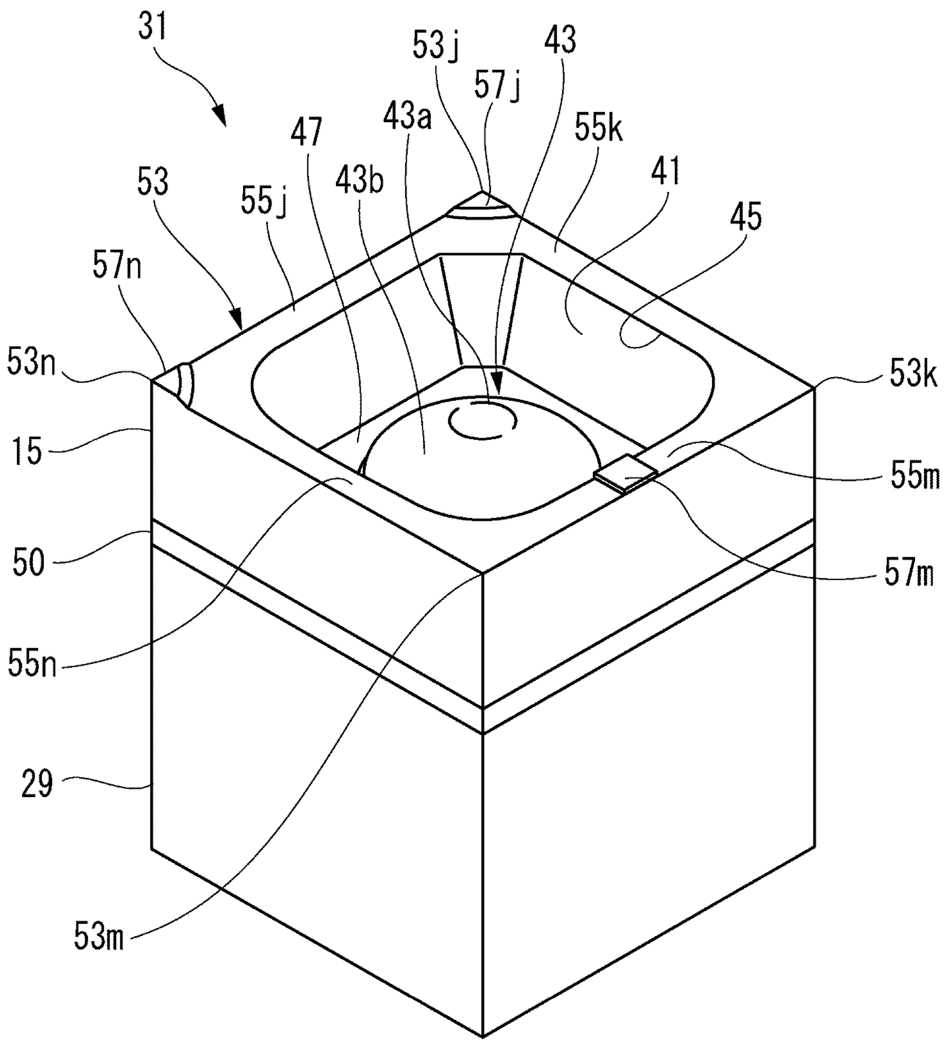
FIG. 13 is a perspective view of a lens according to Modification 2.

FIG. 13 is a perspective view of the lens 15 according to Modification 2. The frame portion 53 according to the present modification includes linear frame portions 55*j*, 55*k*, 55*m*, and 55*n*. The linear frame portion 55*j* corresponds to a linear end surface disposed between a first corner 53*j* and a second corner 53*n* of the frame portion 53. The linear frame portion 55*j* corresponds to a first linear frame portion according to the present modification. The linear frame portion 55*m* corresponds to a linear end surface disposed parallel to the linear frame portion 55*j*. The linear frame portion 55*m* corresponds to a second linear frame portion according to the present modification. The linear frame portion 55*k* corresponds to a linear end surface orthogonal to the linear frame portion 55*j* and the linear frame portion 55*m*. The linear frame portion 55*k* corresponds to a third linear frame portion according to the present modification. The linear frame portion 55*n* corresponds to a linear end surface disposed parallel to the linear frame portion 55*k*. The linear frame portion 55*n* corresponds to a fourth linear frame portion according to the present modification.

The protrusion 57*j* is formed at one end portion of the linear frame portion 55*j*, in other words, at the first corner 53*j* of the frame portion 53. The protrusion 57*j* corresponds to a first protrusion according to the present modification. The protrusion 57*n* is formed at the other end portion of the linear frame portion 55*j*, in other words, at the second corner 53*n* of the frame portion 53. The protrusion 57*n* corresponds to a second protrusion according to the present modification. The protrusion 57*m* is formed at a central portion of the linear frame portion 55*m*. The protrusion 57*m* corresponds to a third protrusion according to the present modification.

In this way, the protrusions 57*j*, 57*m*, and 57*n* are formed in at least a part of at least two parallel linear frame portions among the linear frame portions 55*j*, 55*k*, 55*m*, and 55*n* constituting the frame portion 53. The protrusions 57*j*, 57*m*, and 57*n* are an example of the protrusion portion according to the present modification. For example, the protrusion 57*j* is formed at the one end portion of the linear frame portion 55*j* in a longitudinal direction. The protrusion 57*n* is formed at the other end of the linear frame portion 55*j* in a longitudinal direction. Further, the protrusion 57*m* is formed at the central portion of the linear frame portion 55*m* in a longitudinal direction, parallel to the linear frame portion 55*j*. In this case, the protrusion 57*j* and the protrusion 57*n* can each be formed into a quarter-circular shape, that is, a fan shape. The protrusion 57*m* can be formed in a square shape having one side equal to the end surface width c of the linear frame portion 55*m*. The protrusions 57*j*, 57*m*, and 57*n* may be integrally molded with the lens 15.

In the present modification, the lens 15 and the image sensor 21 can be positioned in parallel by forming the three protrusions 57 at the frame portion 53. In this way, a joining area between the lens 15 and the image sensor 21 by the adhesive 51 can be increased, and an adhesive strength can be further improved. As a result, in the present modification, the lens 15 is less likely to be warped, and deterioration in image quality (unstable image quality) can be prevented.

Modification 3

Figure 14:
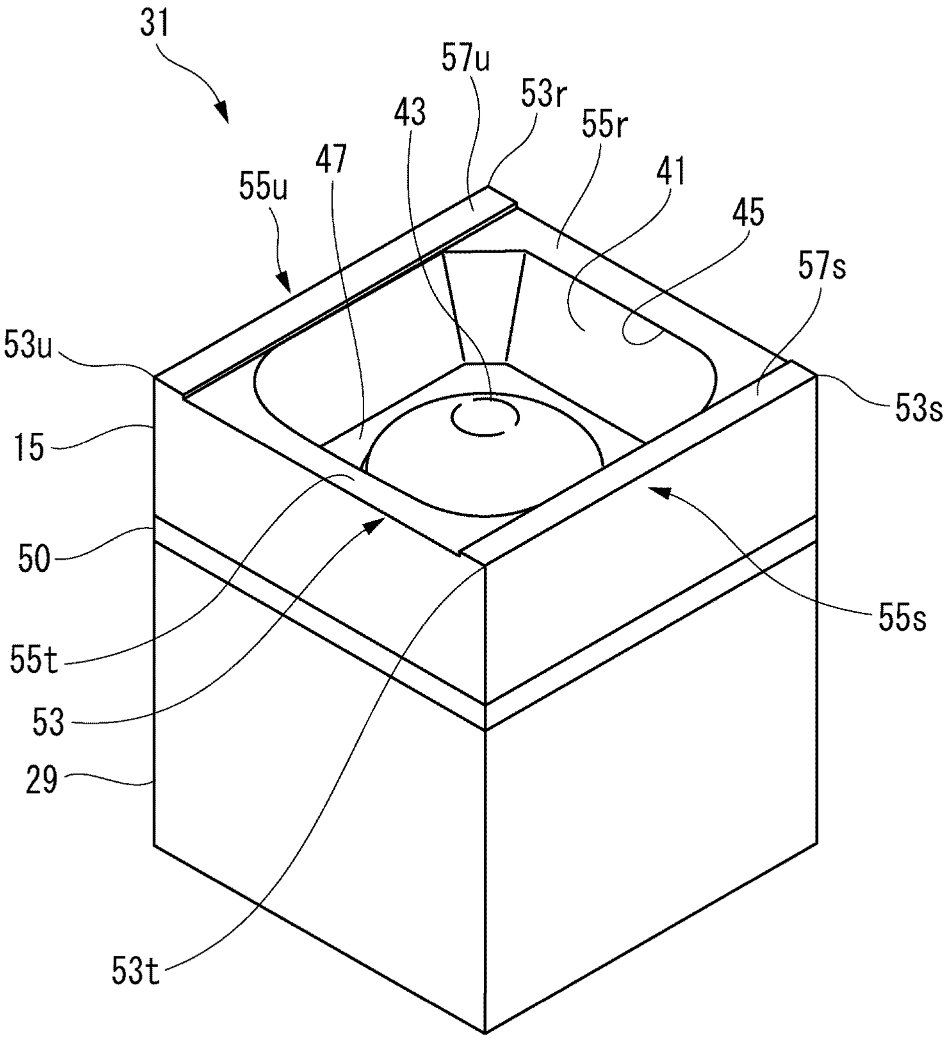
FIG. 14 is a perspective view of a lens according to Modification 3.

FIG. 14 is a perspective view of the lens 15 according to Modification 3. The frame portion 53 according to the present modification includes linear frame portions 55*r*, 55*s*, 55*t*, and 55*u*. The linear frame portion 55*r* corresponds to a linear end surface disposed between a first corner 53*r* and a second corner 53*s* of the frame portion 53. The linear frame portion 55*r* corresponds to a first linear frame portion according to the present modification. The linear frame portion 55*t* corresponds to a linear end surface disposed parallel to the linear frame portion 55*r*. The linear frame portion 55*t* corresponds to a second linear frame portion according to the present modification. The linear frame portion 55*s* corresponds to a linear end surface orthogonal to the linear frame portion 55*r* and the linear frame portion 55*t*. The linear frame portion 55*s* corresponds to a third linear frame portion according to the present modification. The linear frame portion 55*u* corresponds to a linear end surface disposed parallel to the linear frame portion 55*s*. The linear frame portion 55*u* corresponds to a fourth linear frame portion according to the present modification.

The protrusion 57*u* is formed over the entire length of the linear frame portion 55*u*. The protrusion 57*u* corresponds to a first protrusion according to the present modification. The protrusion 57*s* is formed over the entire length of the linear frame portion 55*s*. The protrusion 57*s* corresponds to a second protrusion according to the present modification. In this way, in the present modification, the protrusion 57*u* and the protrusion 57*s* are formed over the entire length in a longitudinal direction of the linear frame portion 55*u* and the linear frame portion 55*s* arranged in parallel in the frame portion 53.

The protrusion 57*u* may not be formed over the entire length of the linear frame portion 55*u* in the longitudinal direction. The same applies to the protrusion 57*s*. For example, the protrusion 57*u* may be formed at the vicinity of a central portion of the linear frame portion 55*u* from one end in the longitudinal direction (that is, from the first corner 53*r* of the frame portion 53 to the central portion of the linear frame portion 55*u*). The protrusion 57*s* may be formed at the vicinity of a central portion of the linear frame portion 55*s* from the other end in the longitudinal direction (that is, from the third corner 53*t* of the frame portion 53 to the central portion of the linear frame portion 55*s*). That is, in the present modification, the protrusion 57*u* is formed to extend in the longitudinal direction of the linear frame portion 55*u*, and the protrusion 57*s* is formed to extend in the longitudinal direction of the linear frame portion 55*s*. The protrusions 57*u* and 57*s* may be integrally molded with the lens 15. The protrusions 57*u* and 57*s* are an example of the protrusion portion according to the present modification.

In the present modification, an application amount of the adhesive 51 can be reduced as compared with a case where the adhesive 51 is applied to the entire periphery of the frame portion 53. In the endoscope 11 according to the present modification, the adhesive 51 is applied only to the two parallel linear frame portions 55. Therefore, it is possible to reduce an amount of the adhesive 51 protruding toward a recess side or an outer shape side, and to prevent the adhesive 51 from protruding into the optical effective area Oa (see FIG. 14C), thereby preventing deterioration in image quality.

As described Modifications 1, 2, and 3, in the endoscope 11, the protrusions 57 are formed in at least a part of at least two parallel linear frame portions 55 among the four linear frame portions 55. More specifically, when the protrusion 57 has a small area, it is preferable to form three or more protrusions 57 at the frame portion 53. Two or more protrusions 57 may be formed at the frame portion 53 as long as the protrusion 57 has a large area. Here, the protrusion 57 having a small area corresponds to the protrusion 57 having an area in which it is difficult to stably maintain parallelism between the second surface 19 and the adhered surface 35 (or the imaging surface 21*a*) when two protrusions 57 are provided. The protrusion 57 having a large area corresponds to a protrusion having an area capable of stably maintaining the parallelism between the second surface 19 and the adhered surface 35 (or the imaging surface 21*a*) even when two protrusions 57 are provided.

Various embodiments have been described above with reference to the drawings, but the present disclosure is not limited thereto. It is apparent to a person skilled in the art that various changes, modifications, substitutions, additions, deletions, and equivalents can be conceived within the scope of the claims, and it is understood that such modifications also belong to the technical scope of the present disclosure. The components in the various embodiments described above may be optionally combined without departing from the gist of the invention.

A part or all of the embodiments described above may be described as the following appendixes, but are not limited thereto.

Appendix 1

An endoscope includes:

an image sensor having an imaging surface; and a lens configured to be adhered to the imaging surface by an adhesive and to image light on the image sensor, and the lens includes

- a light incident surface extending in an orthogonal direction orthogonal to an optical axis direction of the lens,
- a back surface parallel to the light incident surface and facing the imaging surface,
- a recess having an opening formed in the back surface and an in-lens space formed between the opening and the light incident surface, the recess being recessed from the opening toward the light incident surface,
- an emission portion disposed in the in-lens space and configured to emit light from the light incident surface to the imaging surface,
- a frame portion disposed around the opening in the back surface, and
- a protrusion protruding from the frame portion in the optical axis direction and configured to abut on the imaging surface.

Appendix 2

An endoscope includes:

an image sensor including an imaging surface and an element cover glass that covers the imaging surface; and a lens configured to be adhered to the element cover glass by an adhesive and to image light on the image sensor, and the lens includes a light incident surface extending in an orthogonal direction orthogonal to an optical axis direction of the lens, a back surface parallel to the light incident surface and facing the element cover glass, a recess having an opening formed in the back surface and an in-lens space formed between the opening and the light incident surface, the recess being recessed from the opening toward the light incident surface, an emission portion disposed in the in-lens space and configured to emit light from the light incident surface to the imaging surface, a frame portion disposed around the opening in the back surface, and a protrusion protruding from the frame portion in the optical axis direction and configured to abut on the element cover glass.

Appendix 3

In the endoscope according to Appendix 1 or 2, the emission portion includes a top portion disposed between the back surface and the light incident surface with respect to the optical axis direction.

Appendix 4

In the endoscope according to Appendix 3, the emission portion includes a convex curved surface portion protruding in a first direction from the light incident surface toward the back surface with respect to the optical axis direction, and the top portion is disposed on the convex curved surface portion.

Appendix 5

In the endoscope according to Appendix 4, the recess has a bottom surface disposed between the back surface and the light incident surface in the optical axis direction and closer to the light incident surface than the top portion, and the convex curved surface portion protrudes from the bottom surface in the first direction.

Appendix 6

In the endoscope according to Appendix 4 or 5, the convex curved surface portion is a spherical surface.

Appendix 7

In the endoscope according to any one of Appendixes 1 to 6, the imaging surface of the image sensor has a quadrangular shape, and the lens is a quadrangular prism in which each of the light incident surface and the back surface has a quadrangular shape and which extends from the light incident surface to the back surface.

Appendix 8

In the endoscope according to Appendix 7, the protrusion portion includes

- a first protrusion formed at a first corner of the frame portion intersecting a first diagonal line of the back surface,
- a second protrusion formed at a second corner of the frame portion intersecting the first diagonal line,
- a third protrusion formed at a third corner of the frame portion intersecting a second diagonal line of the back surface that intersects the first diagonal line, and
- a fourth protrusion formed at a fourth corner of the frame portion intersecting the second diagonal line.

Appendix 9

In the endoscope according to Appendix 8, each of the first protrusion, the second protrusion, the third protrusion, and the fourth protrusion has a fan shape when viewed in the first direction from the back surface toward the light incident surface with respect to the optical axis direction.

Appendix 10

In the endoscope according to Appendix 7, the frame portion includes a first linear frame portion disposed between a first corner of the back surface and a second corner of the back surface, a second linear frame portion disposed parallel to the first linear frame portion, a third linear frame portion orthogonal to the first linear frame portion and the second linear frame portion, and a fourth linear frame portion disposed parallel to the third linear frame portion, and the protrusion portion includes a first protrusion formed at the first linear frame portion, a second protrusion formed at the second linear frame portion, a third protrusion formed at the third linear frame portion, and a fourth protrusion formed at the fourth linear frame portion.

Appendix 11

In the endoscope according to Appendix 10, the opening portion has a quadrangular shape similar to the back surface, the first protrusion is formed at a central portion of the first linear frame portion, the second protrusion is formed at a central portion of the second linear frame portion, the third protrusion is formed at a central portion of the third linear frame portion, and the fourth protrusion is formed at a central portion of the fourth linear frame portion.

Appendix 12

In the endoscope according to Appendix 10 or 11, each of the first protrusion, the second protrusion, the third protrusion, and the fourth protrusion has a quadrangular shape when viewed in the first direction from the back surface toward the light incident surface with respect to the optical axis direction.

Appendix 13

In the endoscope according to Appendix 7, the opening has a quadrangular shape similar to the back surface, the frame portion includes a first linear frame portion disposed between a first corner of the back surface and a second corner of the back surface, a second linear frame portion disposed parallel to the first linear frame portion, a third linear frame portion orthogonal to the first linear frame portion and the second linear frame portion, and a fourth linear frame portion disposed parallel to the third linear frame portion, and the protrusion portion includes a first protrusion formed at the first corner, a second protrusion formed at the second corner, and a third protrusion formed at the second linear frame portion.

Appendix 14

In the endoscope according to Appendix 13, each of the first protrusion and the second protrusion has a fan shape when viewed in the first direction from the back surface toward the light incident surface with respect to the optical axis direction, and the third protrusion has a quadrangular shape when viewed in the first direction.

Appendix 15

In the endoscope according to Appendix 7, the frame portion includes a first linear frame portion disposed between a first corner of the back surface and a second corner of the back surface, a second linear frame portion disposed parallel to the first linear frame portion, a third linear frame portion orthogonal to the first linear frame portion and the second linear frame portion, and a fourth linear frame portion disposed parallel to the third linear frame portion, and the protrusion portion includes a first protrusion formed to extend in a longitudinal direction of the third linear frame portion and a second protrusion formed to extend in a longitudinal direction of the fourth linear frame portion.

Appendix 16

In the endoscope according to any one of Appendixes 1 to 15, the frame portion is a frame-shaped end surface disposed on the same plane as the back surface.

Appendix 17

A method for producing an endoscope including: an image sensor having an imaging surface, and a lens including a frame portion disposed on a back surface facing the imaging surface and a protrusion portion formed at the frame portion, the lens being configured to be adhered to the imaging surface by an adhesive and to image light on the image sensor, the method including:

an application step of applying the adhesive to either the frame portion or the imaging surface;

an optical axis alignment step of aligning an optical axis of the image sensor with an optical axis of the lens;

an abutment step of abutting the lens on the imaging surface via the protrusion portion; and a curing step of curing the adhesive.

Appendix 18

A method for producing an endoscope including: an image sensor including an imaging surface and an element cover glass that covers the imaging surface, and a lens including a frame portion disposed on a back surface facing the element cover glass and a protrusion portion formed at the frame portion, the lens being configured to be adhered to the element cover glass by an adhesive, and to image light on the image sensor, the method including:

an application step of applying the adhesive to either the frame portion or the element cover glass;

an optical axis alignment step of aligning an optical axis of the image sensor with an optical axis of the lens;

an abutment step of abutting the lens on the element cover glass via the protrusion portion; and a curing step of curing the adhesive.

Appendix 19

An endoscope includes:

a lens formed of a hexahedron in which each surface has a quadrangular outer shape and imaging light is incident onto a quadrangular first surface that is one of the surfaces; and an image sensor configured to be adhered to a second surface of the lens provided parallel to the first surface, and onto which the imaging light is incident, and the lens includes a recess recessed in the second surface, a convex curved surface portion protruding from a bottom surface of the recess to be lower than the second surface and configured to emit the imaging light toward the image sensor, a frame-shaped end surface that is a portion surrounding the recess in the second surface and configured to be fixed to the image sensor via an adhesive, and a plurality of protrusions protruding from the frame-shaped end surface and configured to abut on the image sensor.

Appendix 20

In the endoscope according to Appendix 19, the plurality of protrusions protrude from the frame-shaped end surface at the same height.

Appendix 21

In the endoscope according to Appendix 19, the plurality of protrusions are formed at four corners of the frame-shaped end surface.

Appendix 22

In the endoscope according to Appendix 19, the plurality of protrusions are formed to be spaced apart at a part of four linear end surfaces constituting the frame-shaped end surface.

Appendix 23

In the endoscope according to Appendix 22, the plurality of protrusions are respectively formed at central portions of the four linear end surfaces in longitudinal directions.

Appendix 24

In the endoscope according to Appendix 22, some of the plurality of protrusions are formed at both end portions of one linear end surface in a longitudinal direction, and the rest of the plurality of protrusions are formed at a central portion of a linear end surface parallel to the one linear end surface in a longitudinal direction.

Appendix 25

In the endoscope according to Appendix 22, the plurality of protrusions are respectively formed over the entire lengths of two parallel linear end surfaces in longitudinal directions.

Appendix 26

A method for producing an endoscope including: a lens formed of a hexahedron in which each surface has a quadrangular outer shape and imaging light is incident onto a quadrangular first surface that is one of the surfaces, and an image sensor configured to be mounted on a second surface of the lens provided parallel to the first surface, and onto which the imaging light is incident, the method including:

a holding step of chucking the lens and the image sensor;

an application step of applying an adhesive to either a frame-shaped end surface surrounding a recess recessed in the second surface or an adhered surface of the image sensor;

an optical axis alignment step of aligning an optical axis of the lens with an optical axis of the image sensor;

an abutment step of abutting the lens on the image sensor via a plurality of protrusions formed at the frame-shaped end surface; and a curing step of curing the adhesive.

The present application is based on a priority based on a Japanese patent application filed on Jul. 7, 2021 (Japanese Patent Application No. 2021-113080), and all of the disclosure is incorporated herein.

INDUSTRIAL APPLICABILITY

The present disclosure is useful as an endoscope capable of preventing deterioration in image quality and a method for producing the endoscope.

REFERENCE SIGNS LIST

11: endoscope
13: camera unit
15: lens
17: first surface
19: second surface
21: image sensor
21*a*: imaging surface
31: lens unit
35: adhered surface
41: recess
43: emission portion
47: bottom surface
51: adhesive
53: frame portion
55*a*, 55*b*, 55*c*, 55*d*: linear frame portion
57*a*, 57*b*, 57*c*, 57*d*: protrusion
59: optical axis

The invention claimed is:

1. An endoscope, comprising:

an image sensor having an imaging surface; and a lens configured to be adhered to the imaging surface by an adhesive and to image light on the image sensor, wherein the lens includes a light incident surface extending in an orthogonal direction that is orthogonal to a direction of an optical axis of the lens, a back surface parallel to the light incident surface and facing the imaging surface, a recess having an opening disposed in the back surface and an in-lens space disposed between the opening and the light incident surface, the recess being recessed from the opening toward the light incident surface, an emission portion disposed in the in-lens space and configured to emit light from the light incident surface to the imaging surface, a frame portion disposed around the opening in the back surface, and a protrusion portion that protrudes from a surface of the frame portion in the direction of the optical axis of the lens, wherein a top surface of the protrusion portion abuts the imaging surface, wherein, in the direction of the optical axis of the lens, a height of the protrusion portion from the surface of the frame portion to the top surface of the protrusion portion is in a range of 0.001 mm to 0.005 mm, wherein the protrusion portion is fixed via an adhesive to an adhered surface of the imaging surface to which an adhesive is applied, and wherein the adhered surface is a planar surface that extends perpendicular to the direction of the optical axis of the lens.

2. An endoscope, comprising:

an image sensor including an imaging surface and an element cover glass that covers the imaging surface; and a lens configured to be adhered to the element cover glass by an adhesive and to image light on the image sensor, wherein the lens includes a light incident surface extending in an orthogonal direction that is orthogonal to a direction of an optical axis of the lens, a back surface parallel to the light incident surface and facing the element cover glass, a recess having an opening disposed in the back surface and an in-lens space disposed between the opening and the light incident surface, the recess being recessed from the opening toward the light incident surface, an emission portion disposed in the in-lens space and configured to emit light from the light incident surface to the imaging surface, a frame portion disposed around the opening in the back surface, and a protrusion portion that protrudes from a surface of the frame portion in the direction of the optical axis of the lens, wherein a top surface of the protrusion portion abuts the element cover glass, wherein, in the direction of the optical axis of the lens, a height of the protrusion portion from the surface of the frame portion to the top surface of the protrusion portion is in a range of 0.001 mm to 0.005 mm, wherein the protrusion portion is fixed via an adhesive to an adhered surface of the element cover glass to which an adhesive is applied, and wherein the adhered surface is a planar surface that extends perpendicular to the direction of the optical axis of the lens.

3. The endoscope according to claim 1, wherein the emission portion includes a top portion disposed between the back surface and the light incident surface with respect to the direction of the optical axis of the lens.

4. The endoscope according to claim 3, wherein the emission portion includes a convex curved surface portion protruding in a first direction from the light incident surface toward the back surface with respect to the direction of the optical axis of the lens, and the top portion is disposed on the convex curved surface portion.

5. The endoscope according to claim 4, wherein the recess has a bottom surface disposed between the back surface and the light incident surface in the direction of the optical axis of the lens and closer to the light incident surface than the top portion, and the convex curved surface portion protrudes from the bottom surface in the first direction.

6. The endoscope according to claim 4, wherein the convex curved surface portion is a spherical surface.

7. The endoscope according to claim 1, wherein the imaging surface of the image sensor has a quadrangular shape, and the lens is a quadrangular prism in which each of the light incident surface and the back surface has a quadrangular shape and which extends from the light incident surface to the back surface.

8. The endoscope according to claim 7, wherein the protrusion portion includes a first protrusion formed at a first corner of the frame portion intersecting a first diagonal line of the back surface, a second protrusion formed at a second corner of the frame portion intersecting the first diagonal line, a third protrusion formed at a third corner of the frame portion intersecting a second diagonal line of the back surface that intersects the first diagonal line, and a fourth protrusion formed at a fourth corner of the frame portion intersecting the second diagonal line.

9. The endoscope according to claim 8, wherein each of the first protrusion, the second protrusion, the third protrusion, and the fourth protrusion has a fan shape when viewed in the first direction from the back surface toward the light incident surface with respect to the direction of the optical axis of the lens.

10. The endoscope according to claim 7, wherein the frame portion includes a first linear frame portion disposed between a first corner of the back surface and a second corner of the back surface, a second linear frame portion disposed parallel to the first linear frame portion, a third linear frame portion orthogonal to the first linear frame portion and the second linear frame portion, and a fourth linear frame portion disposed parallel to the third linear frame portion, and the protrusion portion includes a first protrusion formed at the first linear frame portion, a second protrusion formed at the second linear frame portion, a third protrusion formed at the third linear frame portion, and a fourth protrusion formed at the fourth linear frame portion.

11. The endoscope according to claim 10, wherein the opening has a quadrangular shape similar to the back surface, the first protrusion is formed at a central portion of the first linear frame portion, the second protrusion is formed at a central portion of the second linear frame portion, the third protrusion is formed at a central portion of the third linear frame portion, and the fourth protrusion is formed at a central portion of the fourth linear frame portion.

12. The endoscope according to claim 10, wherein each of the first protrusion, the second protrusion, the third protrusion, and the fourth protrusion has a quadrangular shape when viewed in the first direction from the back surface toward the light incident surface with respect to the direction of the optical axis of the lens.

13. The endoscope according to claim 7, wherein the opening has a quadrangular shape similar to the back surface, the frame portion includes a first linear frame portion disposed between a first corner of the back surface and a second corner of the back surface, a second linear frame portion disposed parallel to the first linear frame portion, a third linear frame portion orthogonal to the first linear frame portion and the second linear frame portion, and a fourth linear frame portion disposed parallel to the third linear frame portion, and the protrusion portion includes a first protrusion formed at the first corner, a second protrusion formed at the second corner, and a third protrusion formed at the second linear frame portion.

14. The endoscope according to claim 13, wherein each of the first protrusion and the second protrusion has a fan shape when viewed in the first direction from the back surface toward the light incident surface with respect to the direction of the optical axis of the lens, and the third protrusion has a quadrangular shape when viewed in the first direction.

15. The endoscope according to claim 7, wherein the frame portion includes a first linear frame portion disposed between a first corner of the back surface and a second corner of the back surface, a second linear frame portion disposed parallel to the first linear frame portion, a third linear frame portion orthogonal to the first linear frame portion and the second linear frame portion, and a fourth linear frame portion disposed parallel to the third linear frame portion, and the protrusion portion includes a first protrusion formed to extend in a longitudinal direction of the third linear frame portion and a second protrusion formed to extend in a longitudinal direction of the fourth linear frame portion.

16. The endoscope according to claim 1, wherein the frame portion is a frame-shaped end surface disposed on the same plane as the back surface.

17. A method for producing an endoscope including: an image sensor having an imaging surface, and a lens including a frame portion disposed on a back surface facing the imaging surface and a protrusion portion formed on a surface of the frame portion, the lens being configured to be adhered to the imaging surface by an adhesive and to image light on the image sensor, the method comprising:

forming the protrusion portion to protrude from the surface of the frame portion in a direction of an optical axis of the lens such that a top surface of the protrusion portion is configured to abut the imaging surface;

in the direction of the optical axis of the lens, providing a height of the protrusion portion from the surface of the frame portion to the top surface of the protrusion portion to be in a range of 0.001 mm to 0.005 mm;

applying the adhesive to the imaging surface;

aligning an optical axis of the image sensor with the optical axis of the lens;

abutting the lens on the imaging surface via the protrusion portion;

fixing the protrusion portion to an adhered surface of the imaging surface to which the adhesive has been applied, the adhered surface being provided as a planar surface that extends perpendicular to the direction of the optical axis of the lens; and curing the adhesive.

18. A method for producing an endoscope including: an image sensor including an imaging surface and an element cover glass that covers the imaging surface, and a lens including a frame portion disposed on a back surface facing the element cover glass and a protrusion portion formed on a surface of the frame portion, the lens being configured to be adhered to the element cover glass by an adhesive, and to image light on the image sensor, the method comprising:

forming the protrusion portion to protrude from the surface of the frame portion in a direction of an optical axis of the lens such that a top surface of the protrusion portion is configured to abut the element cover glass;

in the direction of the optical axis of the lens, providing a height of the protrusion portion from the surface of the frame portion to the top surface of the protrusion portion to be in a range of 0.001 mm to 0.005 mm;

applying the adhesive to the element cover glass;

aligning an optical axis of the image sensor with the optical axis of the lens;

abutting the lens on the element cover glass via the protrusion portion;

fixing the protrusion portion to an adhered surface of the element cover glass to which the adhesive has been applied, the adhered surface being provided as a planar surface that extends perpendicular to the direction of the optical axis of the lens; and curing the adhesive.

* * * * *